US011058769B2

(12) United States Patent
Rinaldi et al.

(10) Patent No.: US 11,058,769 B2
(45) Date of Patent: Jul. 13, 2021

(54) AQUEOUS PHARMACEUTICAL FORMULATION COMPRISING ANTI-PD-L1 ANTIBODY AVELUMAB

(71) Applicants: MERCK PATENT GmbH, Darmstadt (DE); PFIZER INC., New York, NY (US)

(72) Inventors: Gianluca Rinaldi, Monterotondo (IT); Alessandra Del Rio, Rome (IT); Silvia Fratar-Cangeli, Ceprano (IT); Senta Voss, Mainz (DE); Markus Weigandt, Mannheim (DE)

(73) Assignees: MERCK PATENT GMBH, Darmstadt (DE); PFIZER INC., New York, NY (US)

( * ) Notice: Subject to any disclaimer, the term of this patent is extended or adjusted under 35 U.S.C. 154(b) by 0 days.

(21) Appl. No.: 16/060,319

(22) PCT Filed: Dec. 5, 2016

(86) PCT No.: PCT/EP2016/002040
§ 371 (c)(1),
(2) Date: Jun. 7, 2018

(87) PCT Pub. No.: WO2017/097407
PCT Pub. Date: Jun. 15, 2017

(65) Prior Publication Data
US 2018/0369377 A1     Dec. 27, 2018

(30) Foreign Application Priority Data
Dec. 7, 2015  (EP) ................................. 15198233

(51) Int. Cl.
*A61K 39/395* (2006.01)
*C07K 16/28* (2006.01)
*A61K 39/00* (2006.01)

(52) U.S. Cl.
CPC .... *A61K 39/39591* (2013.01); *C07K 16/2827* (2013.01); *A61K 2039/54* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| 9,624,298 B2 * | 4/2017 | Nastri ........................ A61P 1/00 |
| 2006/0088523 A1 * | 4/2006 | Andya ............. A61K 39/39541 424/133.1 |
| 2014/0341917 A1 * | 11/2014 | Nastri .................. A61K 31/513 424/139.1 |
| 2020/0016267 A1 | 1/2020 | Rinaldi |

FOREIGN PATENT DOCUMENTS

| WO | 2007/028050 | 3/2007 | |
| WO | WO2007/076354 | 7/2007 | |
| WO | 2009/126556 | 10/2009 | |
| WO | WO2010/066762 | 6/2010 | |
| WO | 2012/037034 | 3/2012 | |
| WO | WO-2012135408 A1 * | 10/2012 | ....... A61K 39/39591 |
| WO | 2013/079174 | 6/2013 | |
| WO | WO2013/112438 | 8/2013 | |
| WO | 2015/048520 | 4/2015 | |
| WO | 2016/137985 | 9/2016 | |
| WO | 2016/181348 | 11/2016 | |
| WO | 2016/205277 | 12/2016 | |
| WO | WO2016200835 | 12/2016 | |
| WO | 2017/058780 | 4/2017 | |
| WO | WO2017097407 | 4/2017 | |

OTHER PUBLICATIONS

U.S. Appl. No. 62/423,358, filed Nov. 17, 2016, Nuyten et al.
Chumsae, et al., "Comparison of methionine oxidation in thermal stability and chemically stressed samples of a fully human monoclonal antibody," Journal of Chromatography B, 850(1-2):285-294 (2007).
Daugherty, et al., "Formulation and delivery issues for monoclonal antibody therapeutics," Current Trends in Monoclonal Antibody Development and Manufacturing, Springer, US, p. 103-129 (2010).
Lam, et al., "Antioxidants for prevention of methionine oxidation in recombinant monoclonal antibody HER2," Journal of Pharmaceutical Sciences, 86(11):1250-1255 (1997).
Brahmer et al., "Safety and activity of anti-PD-L1 antibody in patients with advanced cancer," N Engl J Med, 366(26):2455-2465 (2012).
Dong et al., "B7-H1, a third member of the B7 family, co-stimulates T-cell proliferation and interleukin-10 secretion," Nat Med 5:1365-1369 (1999).
Dong et al., "Tumor-associated B7-H1 promotes T-cell apoptosis: a potential mechanism of immune evasion," Nat Med, 8:793-800 (2002) [Erratum, Nat Med, 8:1039 (2002)].
Freeman et al., "Engagement of the PD-1 immunoinhibitory receptor by a novel B7 family member leads to negative regulation of lymphocyte activation," J Exp Med, 192:1027-1034 (2000).
Hamid et al., "Safety and tumor responses with lambrolizumab (Anti-PD-1) in melanoma," N Engl J Med, 369:134-44 (2013).
Hamm et al., "Characterization of N-Linked Glycosylation in a Monoclonal Antibody Produced in NS0 Cells Using Capillary Electrophoresis with Laser-Induced Fluorescence Detection," Pharmaceuticals, 6(3):393-406 (2013).
Harvey et al., "Proposal for a Standard System for Drawing Structural Diagrams of N- and O-Linked Carbohydrates and Related Compounds," Proteomics, 9(15):3796-3801 (2009).
Herbst et al., "Predictive correlates of response to the anti-PD-L1 antibody MPDL3280A in cancer patients," Nature, 515:563-567 (2014).

(Continued)

*Primary Examiner* — Yunsoo Kim
(74) *Attorney, Agent, or Firm* — Haley Guiliano LLP; James F. Haley, Jr.

(57) ABSTRACT

The present invention relates to a novel anti-PD-L1 antibody formulation. In particular, the invention relates to an aqueous pharmaceutical formulation of the anti-PD-L1 antibody Avelumab.

40 Claims, 21 Drawing Sheets

Figure 3:
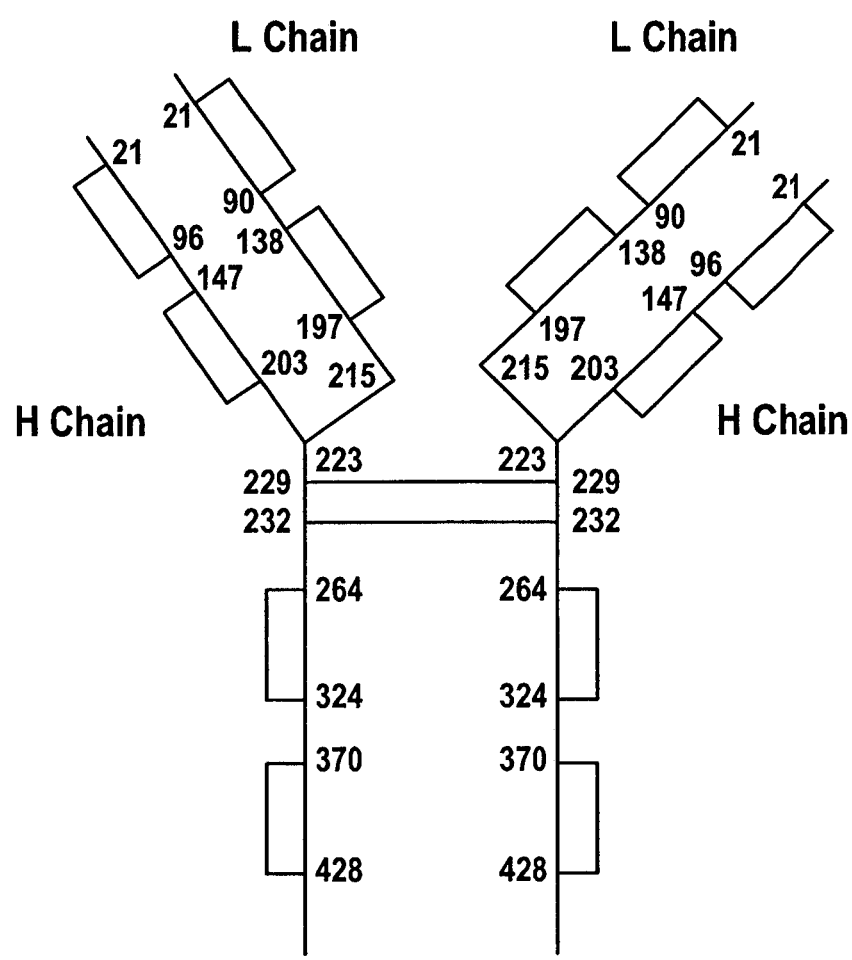

Specification includes a Sequence Listing.

(56) References Cited

OTHER PUBLICATIONS

International Search Report dated Mar. 10, 2017, issued in PCT/EP2016/002040.
Iwai et al., "Involvement of PD-L1 on tumor cells in the escape from host immune system and tumor immunotherapy by PD-L1 blockade," *Proc Natl Acad Sci USA*, 99(19):12293-12297 (2002).
Latchman et al., "PD-L2 is a second ligand for PD-1 and inhibits T cell activation," *Nat Immunol*, 2(3):261-268 (2001).
Okpala, "Investigational Selectin-Targeted Therapy of Sickle Cell Disease," *Expert Opinion on Investigational Drugs*, 24(2):229-238 (2015).
Topalian et al., "Targeting the PD-1/B7-H1(PD-L1) pathway to activate anti-tumor immunity," *Curr Opin Immunol*, 24(2):207-212 (2012).
Topalian et al., "Safety, activity, and immune correlates of anti-PD-1 antibody in cancer," *N Engl J Med*, 366(26):2443-2454 (2012).

\* cited by examiner

Fig. 1a

Heavy chain sequence of Avelumab - SEQ ID NO:1

EVQLLESGGGLVQPGGSLRLSCAASGFTFSSYIMMWVRQAPGKGLEWVSSIYPSG
GITFYADTVKGRFTISRDNSKNTLYLQMNSLRAEDTAVYYCARIKLGTVTTVDYWG
QGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSC
DKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLS
LSPGK

Fig. 1b

Heavy chain sequence of Avelumab, lacking the C-terminal K - SEQ ID NO:2

EVQLLESGGGLVQPGGSLRLSCAASGFTFSSYIMMWVRQAPGKGLEWVSSIYPSG
GITFYADTVKGRFTISRDNSKNTLYLQMNSLRAEDTAVYYCARIKLGTVTTVDYWG
QGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSC
DKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLS
LSPG

Fig. 2

Light chain sequence of Avelumab - SEQ ID NO:3

QSALTQPASVSGSPGQSITISCTGTSSDVGGYNYVSWYQQHPGKAPKLMIYDVSN
RPSGVSNRFSGSKSGNTASLTISGLQAEDEADYYCSSYTSSSTRVFGTGTKVTVLG
QPKANPTVTLFPPSSEELQANKATLVCLISDFYPGAVTVAWKADGSPVKAGVETTK
PSKQSNNKYAASSYLSLTPEQWKSHRSYSCQVTHEGSTVEKTVAPTECS

Fig. 10
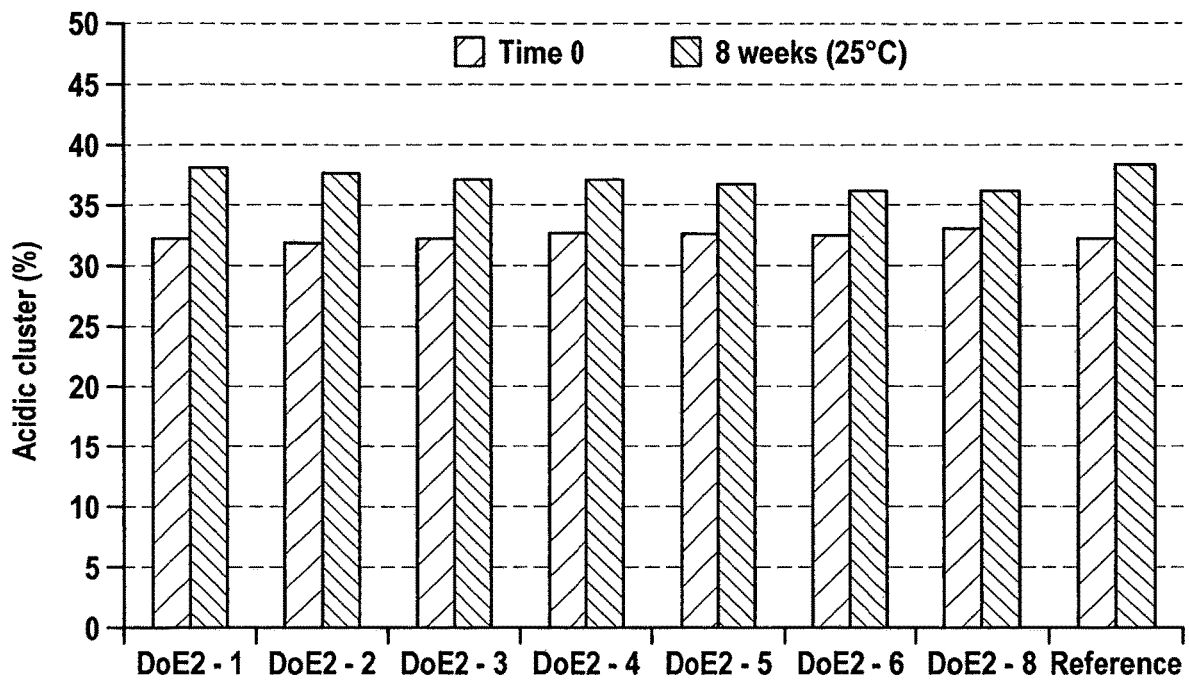
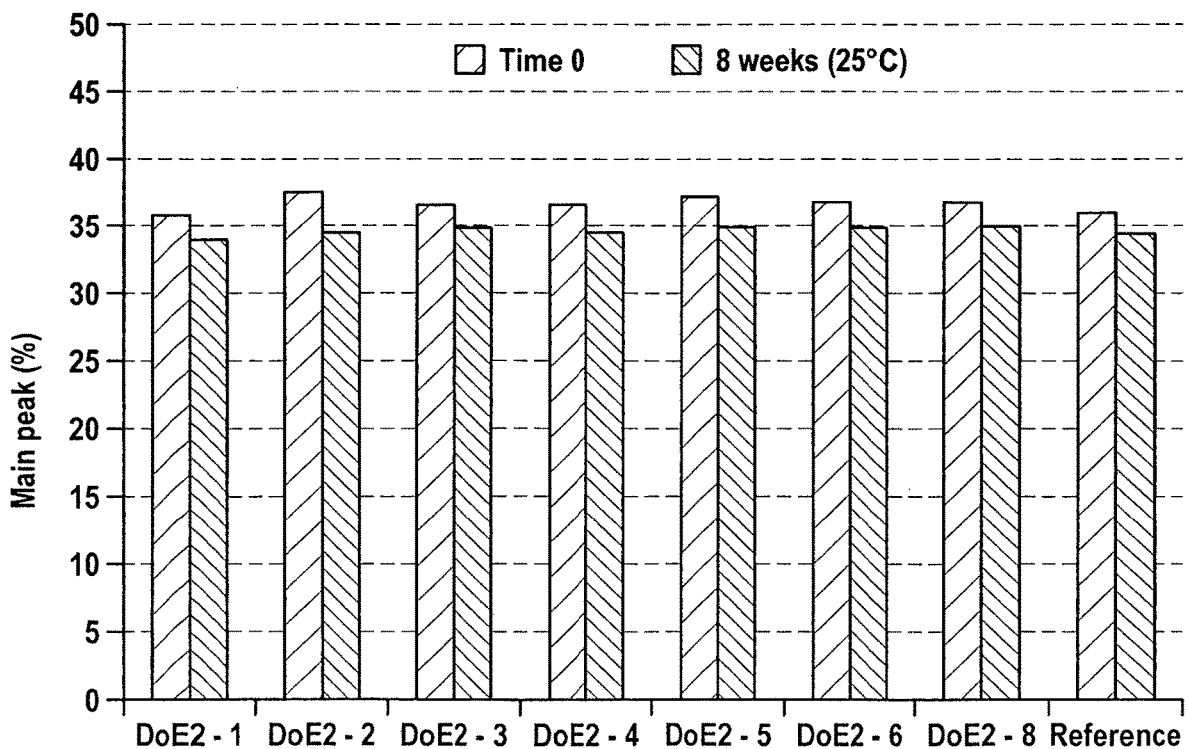

SEQUENCE LISTING

```
<160> NUMBER OF SEQ ID NOS: 3

<210> SEQ ID NO 1
<211> LENGTH: 450
<212> TYPE: PRT
<213> ORGANISM: Artificial Sequence
<220> FEATURE:
<223> OTHER INFORMATION: Heavy chain sequence of Avelumab

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 449
<212> TYPE: PRT
```

<213> ORGANISM: Artificial Sequence
<220> FEATURE:
<223> OTHER INFORMATION: Heavy chain sequence of Avelumab, lacking the
C-terminal K

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

-continued

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 3
<211> LENGTH: 216
<212> TYPE: PRT
<213> ORGANISM: Artificial Sequence
<220> FEATURE:
<223> OTHER INFORMATION: Light chain sequence of Avelumab

<400> SEQUENCE: 3

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

AQUEOUS PHARMACEUTICAL FORMULATION COMPRISING ANTI-PD-L1 ANTIBODY AVELUMAB

This application is the U.S. national phase entry of International Application No. PCT/EP2016/002040, filed Dec. 5, 2016, which claims the benefit of and priority from European Application No. 15198233.7 filed Dec. 7, 2015. The foregoing applications are incorporated herein by reference in their entireties.

The present invention relates to a novel anti-PD-L1 antibody formulation. In particular, the invention relates to an aqueous pharmaceutical formulation of the anti-PD-L1 antibody Avelumab.

BACKGROUND OF THE INVENTION

The programmed death 1 (PD-1) receptor and PD-1 ligands 1 and 2 (PD-L1, PD-L2) play integral roles in immune regulation. Expressed on activated T cells, PD-1 is activated by PD-L1 and PD-L2 expressed by stromal cells, tumor cells, or both, initiating T-cell death and localized immune suppression (Dong H, Zhu G, Tamada K, Chen L. B7-H1, a third member of the B7 family, co-stimulates T-cell proliferation and interleukin-10 secretion. Nat Med 1999; 5:1365-69; Freeman G J, Long A J, Iwai Y, et al. Engagement of the PD-1 immunoinhibitory receptor by a novel B7 family member leads to negative regulation of lymphocyte activation. J Exp Med 2000; 192:1027-34; Dong H, Strome S E, Salomao D R, et al. Tumor-associated B7-H1 promotes T-cell apoptosis: a potential mechanism of immune evasion. Nat Med 2002; 8:793-800. [Erratum, Nat Med 2002; 8:1039; Topalian S L, Drake C G, Pardoll D M. Targeting the PD-1/B7-H1 (PD-L1) pathway to activate anti-tumor immunity. Curr Opin Immunol 2012; 24:207-12), potentially providing an immune-tolerant environment for tumor development and growth. Conversely, inhibition of this interaction can enhance local T-cell responses and mediate antitumor activity in nonclinical animal models (Dong H, Strome S E, Salomao D R, et al. Nat Med 2002; 8:793-800. [Erratum, Nat Med 2002; 8:1039; Iwai Y, Ishida M, Tanaka Y, et al. Involvement of PD-L1 on tumor cells in the escape from host immune system and tumor immunotherapy by PD-L1 blockade. Proc Natl Acad Sci USA 2002; 99:12293-97). In the clinical setting, treatment with antibodies that block the PD-1-PD-L1 interaction have been reported to produce objective response rates of 7% to 38% in patients with advanced or metastatic solid tumors, with tolerable safety profiles (Hamid O, Robert C, Daud A, et al. Safety and tumor responses with lambrolizumab (Anti-PD-1) in melanoma. N Engl J Med 2013; 369:134-44; Brahmer J R, Tykodi S S, Chow L Q, et al. Safety and activity of anti-PD-L1 antibody in patients with advanced cancer. N Engl J Med 2012; 366(26):2455-65; Topalian S L, Hodi F S, Brahmer J R, et al. Safety, activity, and immune correlates of anti-PD-1 antibody in cancer. N Engl J Med 2012; 366(26):2443-54; Herbst R S, Soria J-C, Kowanetz M, et al. Predictive correlates of response to the anti-PD-L1 antibody MPDL3280A in cancer patients. Nature 2014; 515:563-67). Notably, responses appeared prolonged, with durations of 1 year or more for the majority of patients.

Avelumab (also known as MSB0010718C) is a fully human monoclonal antibody of the immunoglobulin (Ig) G1 isotype. Avelumab selectively binds to PD-L1 and competitively blocks its interaction with PD-1.

Compared with anti-PD-1 antibodies that target T-cells, Avelumab targets tumor cells, and therefore is expected to have fewer side effects, including a lower risk of autoimmune-related safety issues, as blockade of PD-L1 leaves the PD-L2-PD-1 pathway intact to promote peripheral self-tolerance (Latchman Y, Wood C R, Chernova T, et al. PD-L1 is a second ligand for PD-1 and inhibits T cell activation. Nat Immunol 2001; 2(3):261-68).

Avelumab is currently being tested in the clinic in a number of cancer types including non-small cell lung cancer, urothelial carcinoma, mesothelioma, Merkel cell carcinoma, gastric or gastroesophageal junction cancer, ovarian cancer, and breast cancer.

The amino acid sequences of Avelumab and sequence variants and antigen binding fragments thereof, are disclosed in WO2013079174, where the antibody having the amino acid sequence of Avelumab is referred to as A09-246-2. Also disclosed are methods of manufacturing and certain medical uses.

Further medical uses of Avelumab are described in WO2016137985, PCT/IB2016/052748, PCT/US2016/037498, PCT/US2016/053939, U.S. patent application Ser. No. 62/341,921.

WO2013079174 also describes in section 2.4 a human aqueous formulation of an antibody having the amino acid sequence of Avelumab. This formulation comprises the antibody in a concentration of 10 mg/ml, methionine as an antioxidant and has a pH of 5.5.

A formulation study for an aglycosylated anti-PD-L1 antibody of the IgG1 type is described in WO2015048520, where a formulation with a pH of 5.8 was selected for clinical studies.

DESCRIPTION OF THE INVENTION

As Avelumab is generally delivered to a patient via intravenous infusion, and is thus provided in an aqueous form, the present invention relates to further aqueous formulations that are suitable to stabilize Avelumab with its post-translational modifications, and at higher concentrations as disclosed in WO2013079174.

FIG. 1a (SEQ ID NO:1) shows the full length heavy chain sequence of Avelumab, as expressed by the CHO cells used as the host organism.

It is frequently observed, however, that in the course of antibody production the C-terminal lysine (K) of the heavy chain is cleaved off. Located in the Fc part, this modification has no influence on the antibody—antigen binding. Therefore, in some embodiments the C-terminal lysine (K) of the heavy chain sequence of Avelumab is absent. The heavy chain sequence of Avelumab without the C-terminal lysine is shown in FIG. 1b (SEQ ID NO:2).

FIG. 2 (SEQ ID NO:3) shows the full length light chain sequence of Avelumab.

A post-translational modification of high relevance is glycosylation.

Most of the soluble and membrane-bound proteins that are made in the endoplasmatic reticulum of eukaryotic cells undergo glycosylation, where enzymes called glycosyltransferases attach one or more sugar units to specific glycosylation sites of the proteins. Most frequently, the points of attachment are $NH_2$ or OH groups, leading to N-linked or O-linked glycosylation.

This applies also to proteins, such as antibodies, which are recombinantly produced in eukaryotic host cells. Recombinant IgG antibodies contain a conserved N-linked glycosylation site at a certain asparagine residue of the Fc region in the CH2 domain. There are many known physical functions of N-linked glycosylation in an antibody such as affecting its solubility and stability, protease resistance, binding to Fc receptors, cellular transport and circulatory half-life in vivo (Hamm M. et al., Pharmaceuticals 2013, 6, 393-406). IgG antibody N-glycan structures are predominantly biantennary complex-type structures, comprising b-D-N-acetylglucosamine (GlcNac), mannose (Man) and frequently galactose (Gal) and fucose (Fuc) units.

In Avelumab the single glycosylation site is Asn300, located in the CH2 domain of both heavy chains. Details of the glycosylation are described in Example 1.

Since glycosylation affects the solubility and stability of an antibody, it is prudent to take this parameter into account when a stable, pharmaceutically suitable formulation of the antibody is to be developed.

Surprisingly, it has been found by the inventors of the present patent application that it is possible to stabilize Avelumab, fully characterized by its amino acid sequence and its post-translational modifications, in a number of aqueous formulations without the presence of an antioxidant, at pH values as low as 5.2.

FIGURES

Figure 8:
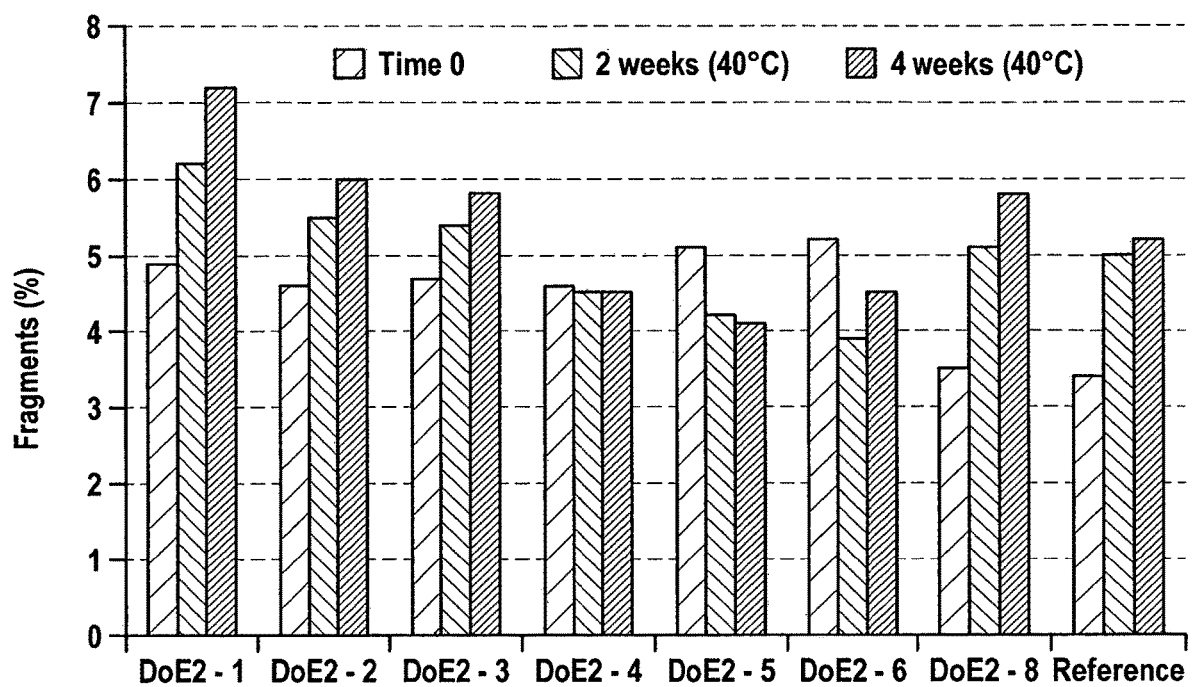
Figure 9:
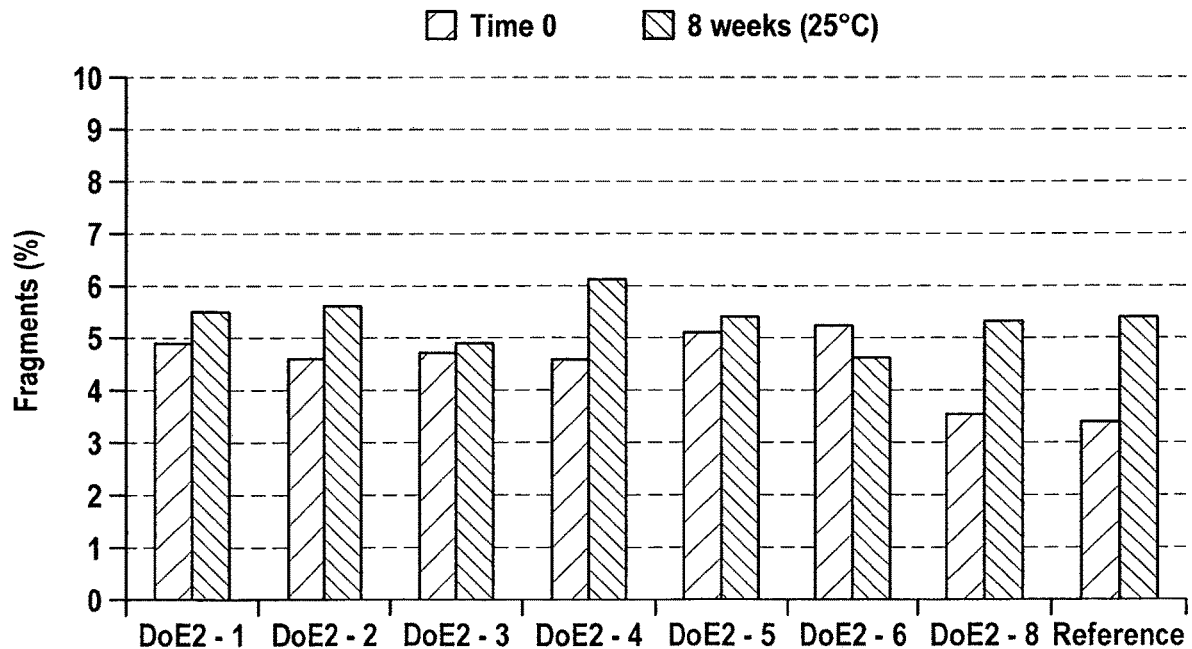
Figure 11:
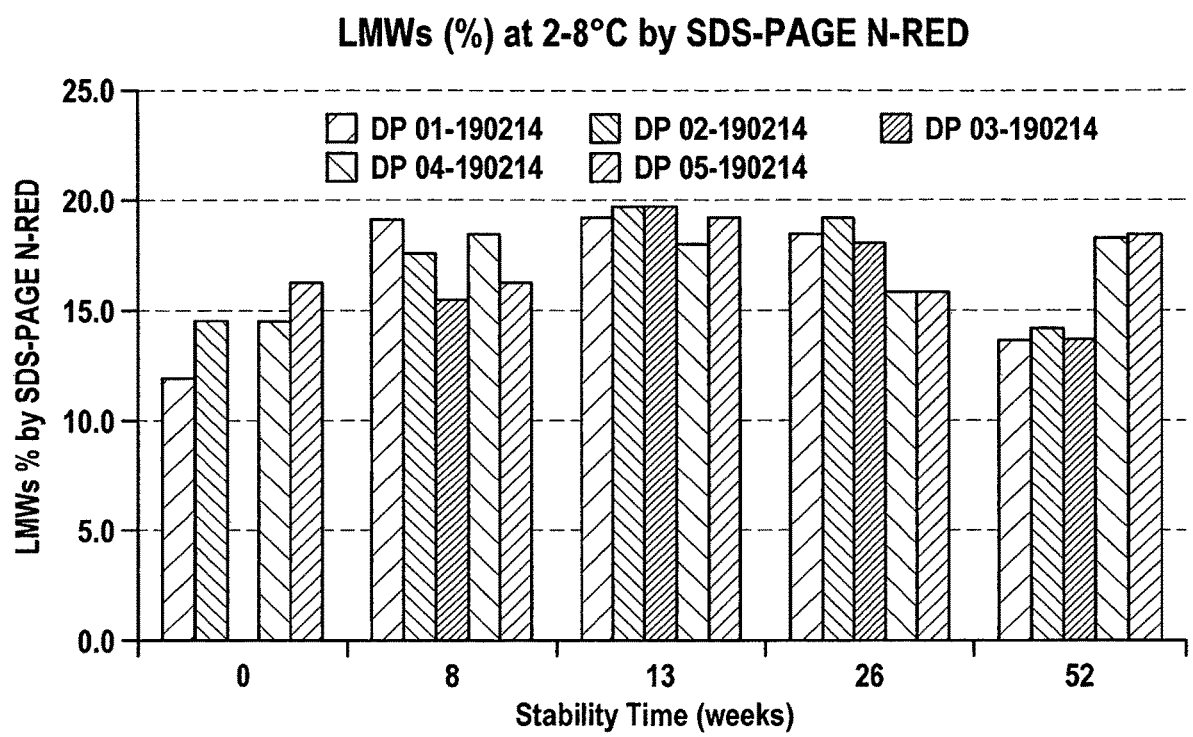
Figure 12:
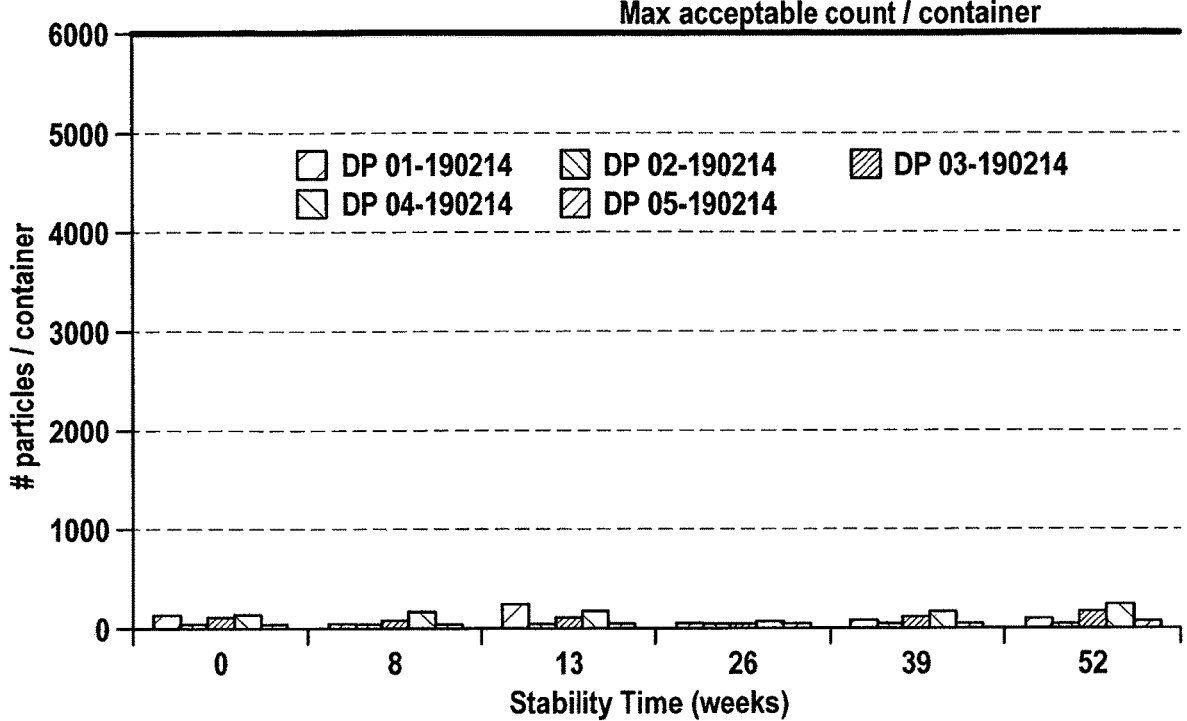
Figure 13:
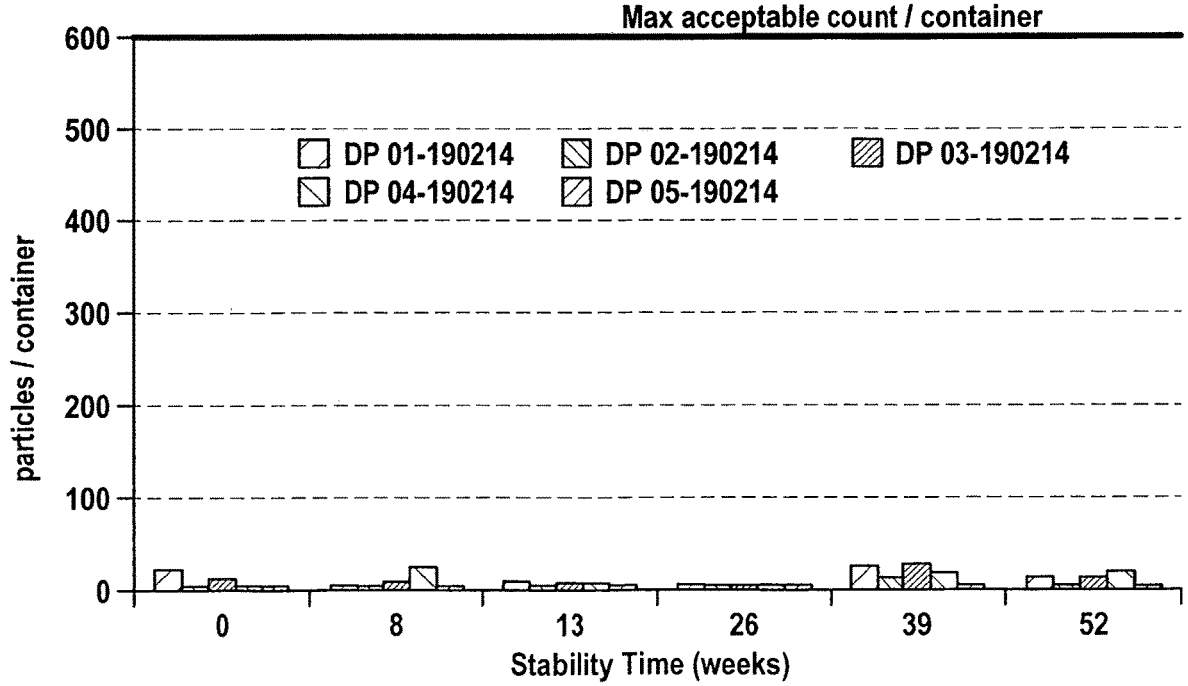
Figure 14:
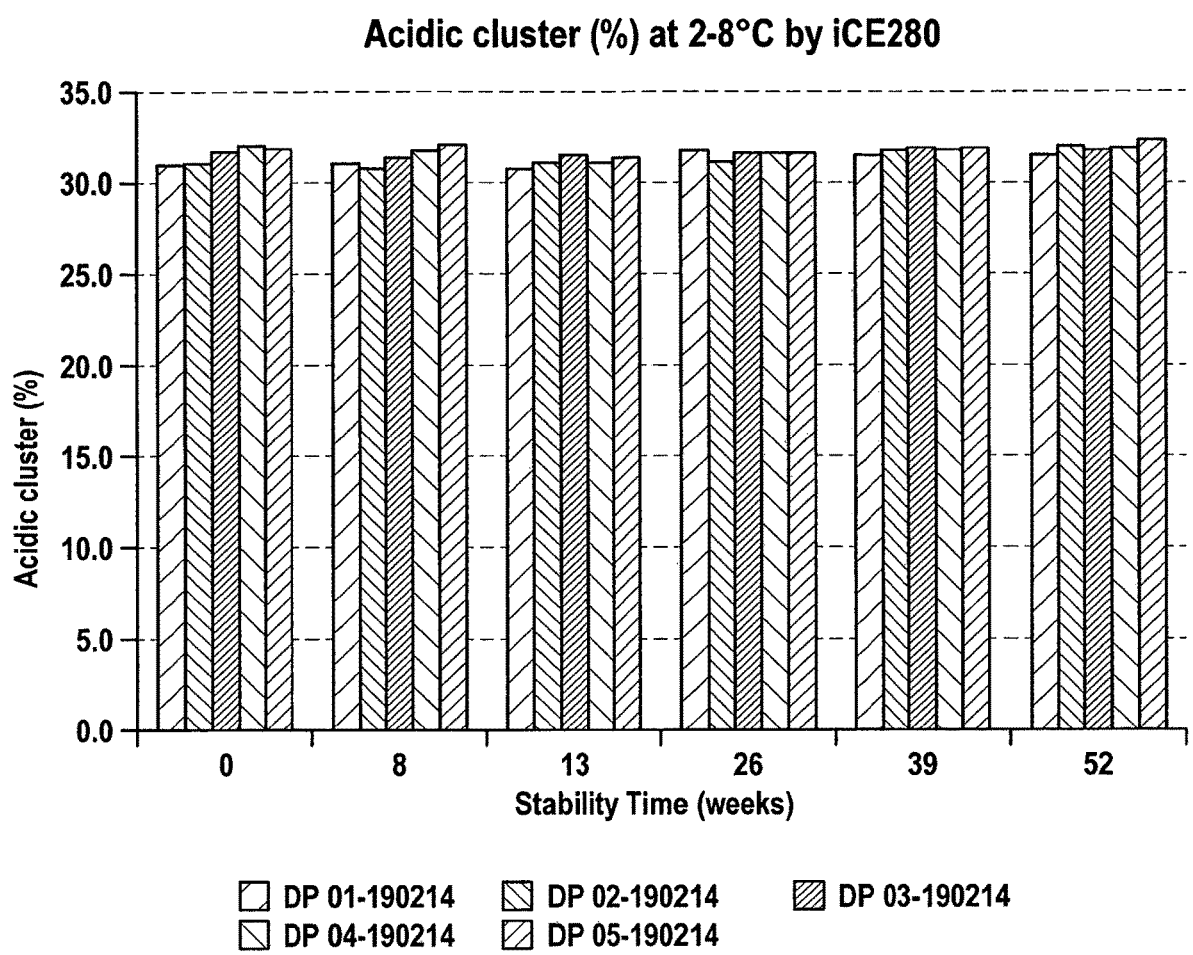
Figure 15:
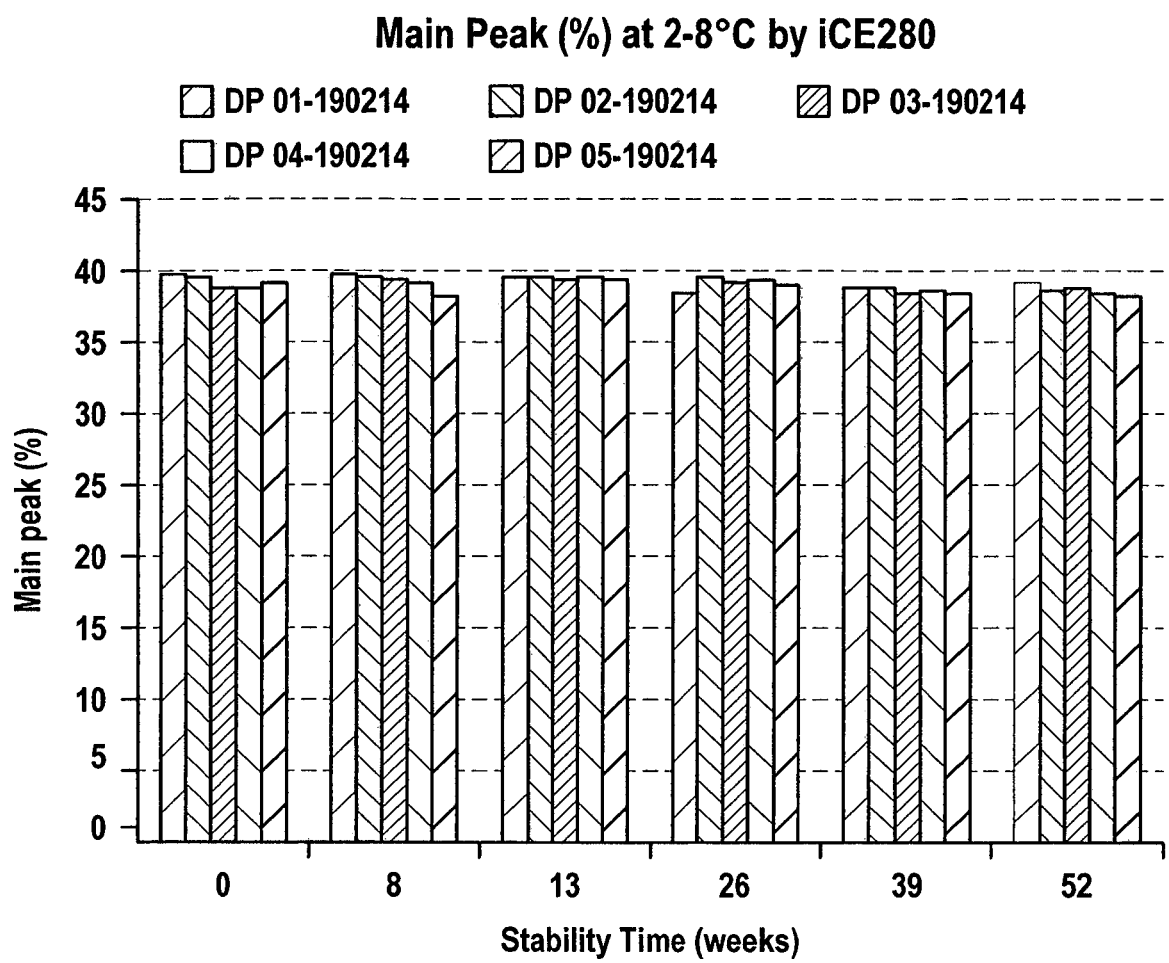
Figure 16:
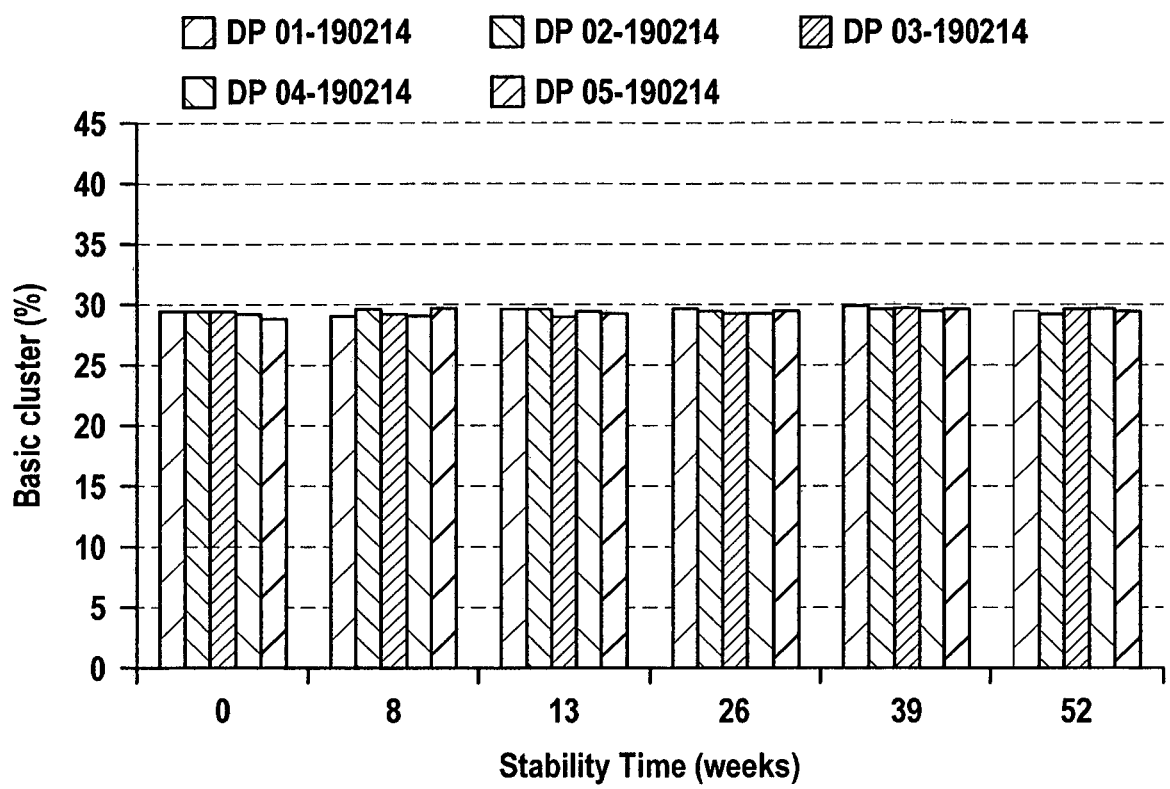
Figure 17:
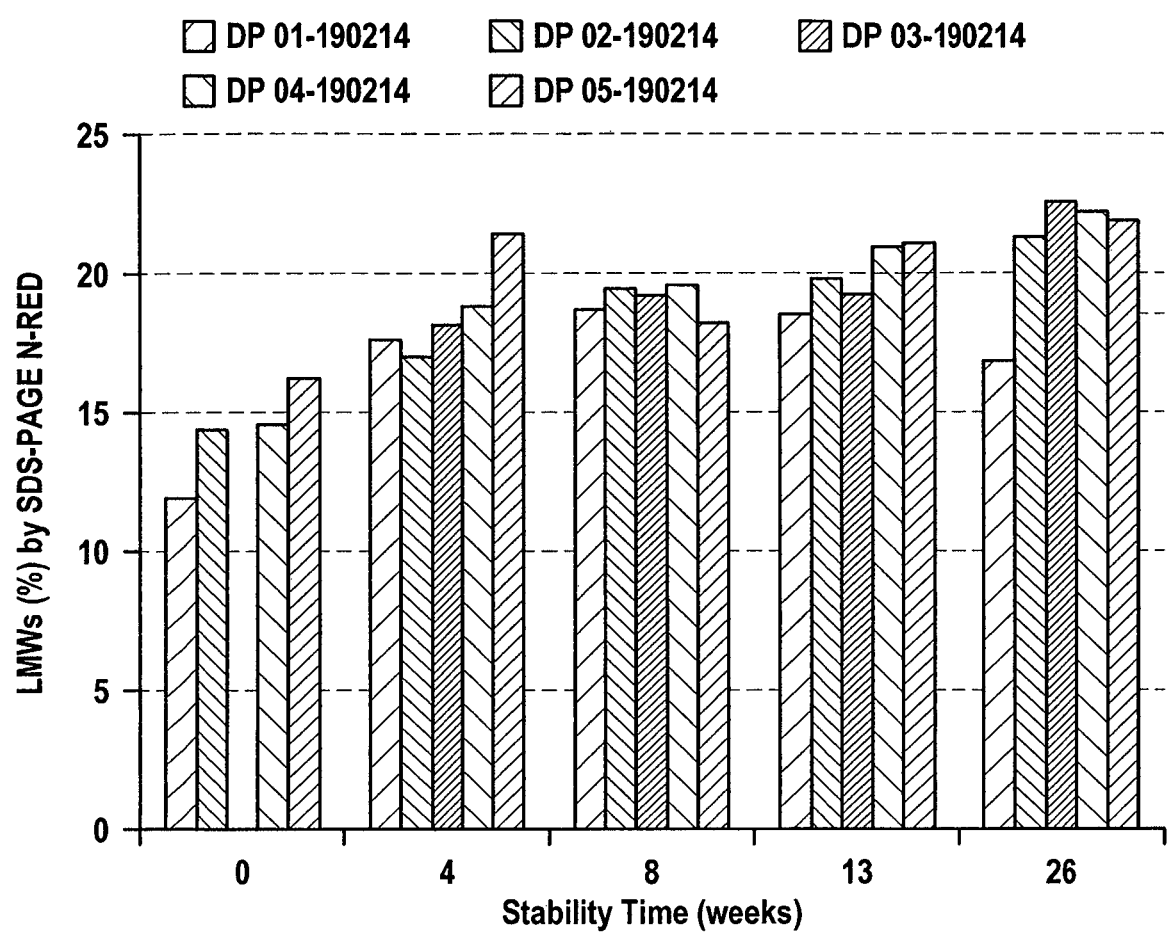
Figure 18:
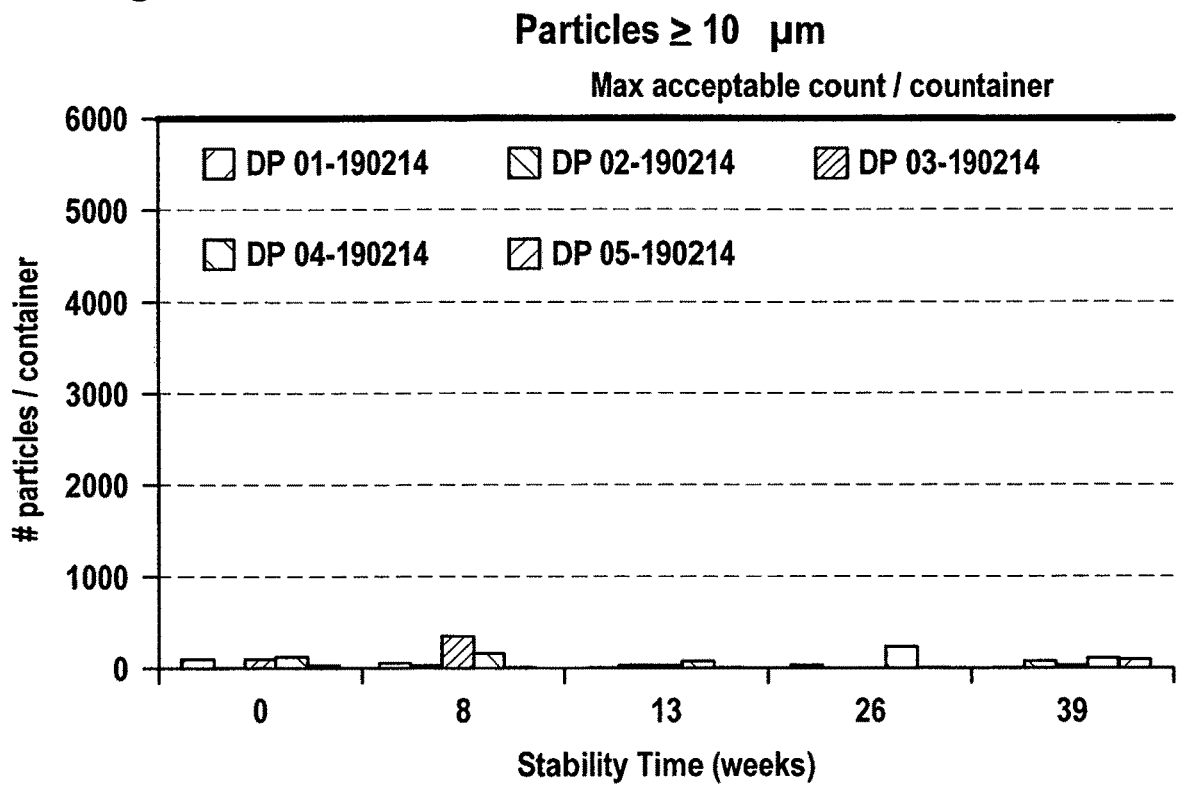
Figure 19:
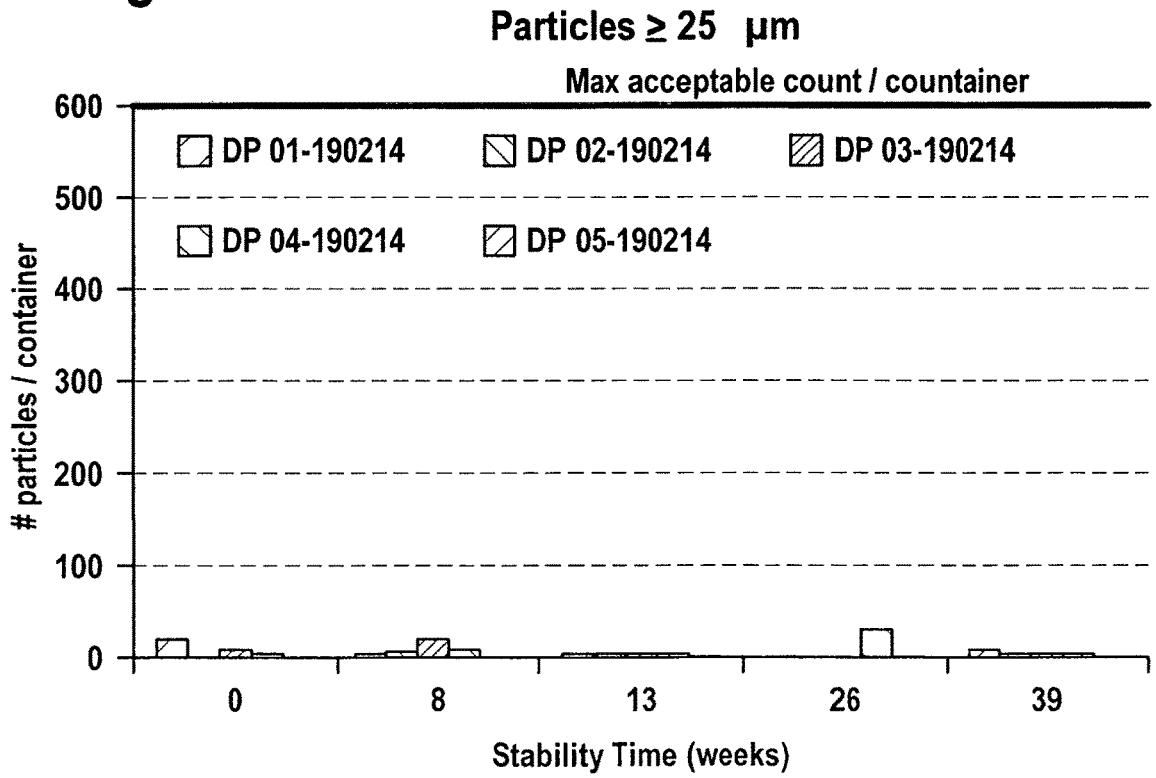
Figure 20:
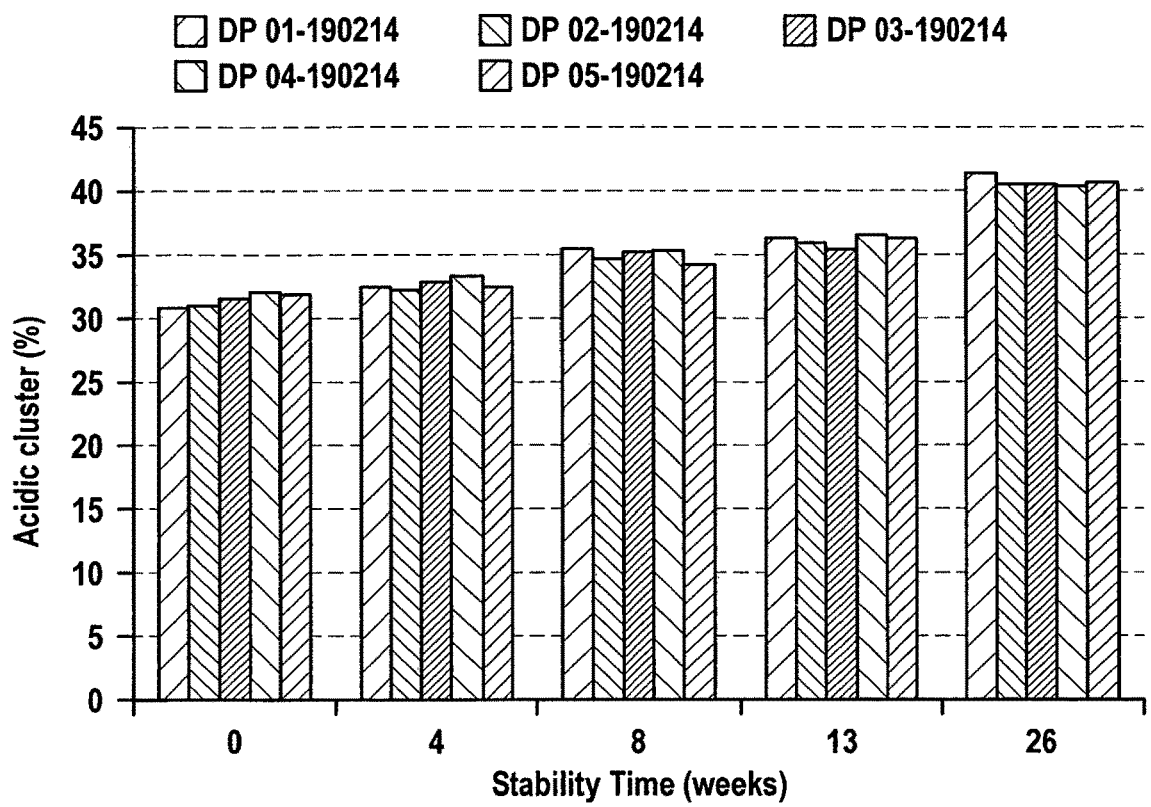
Figure 21:
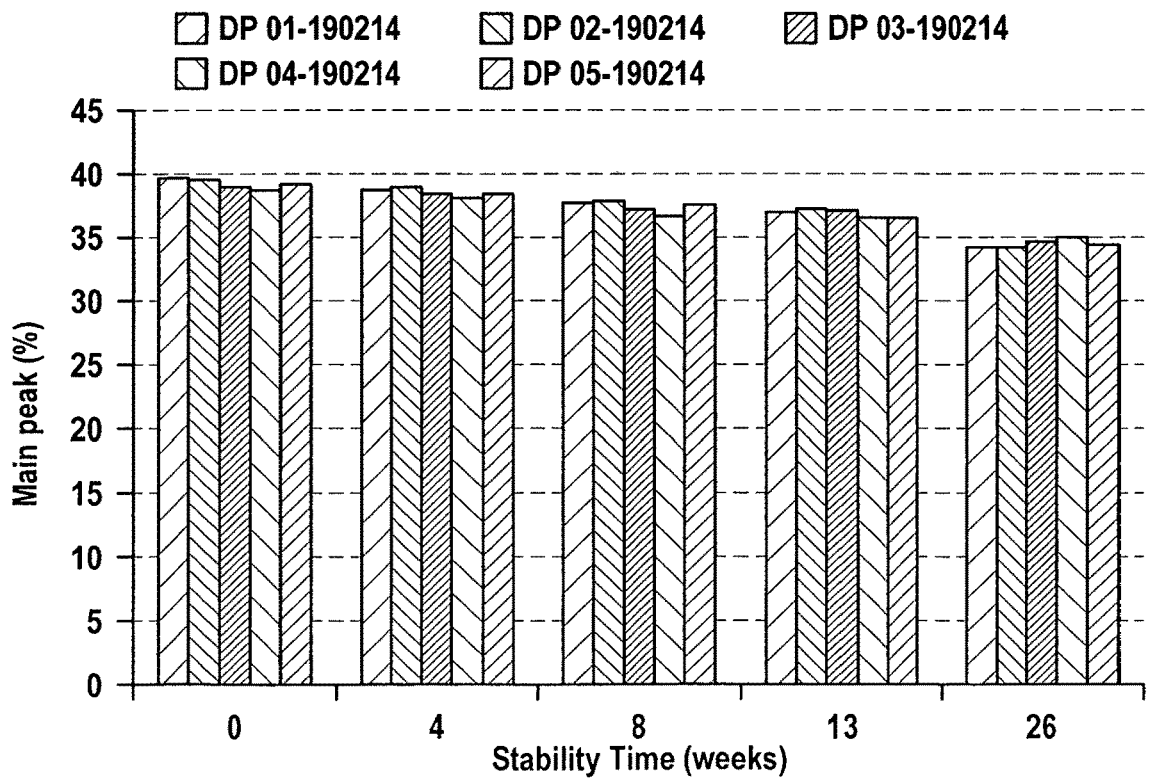
Figure 22:
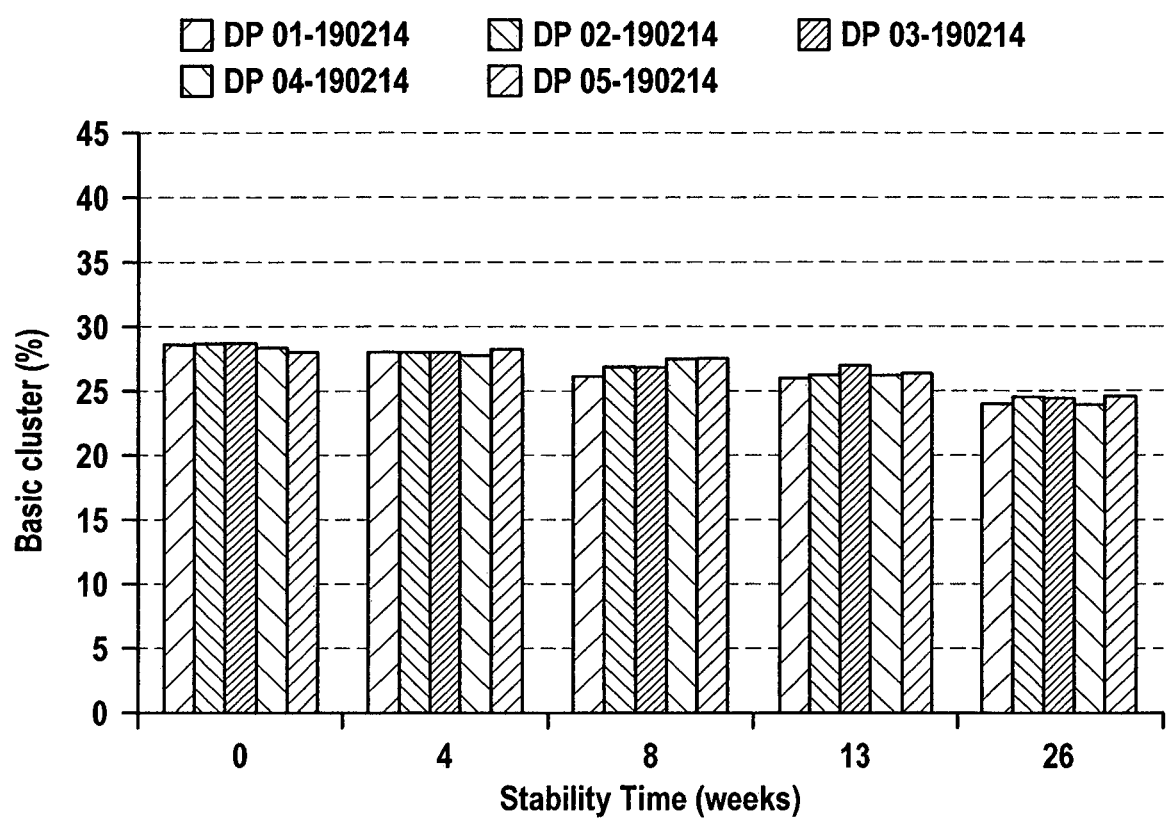
Figure 23:
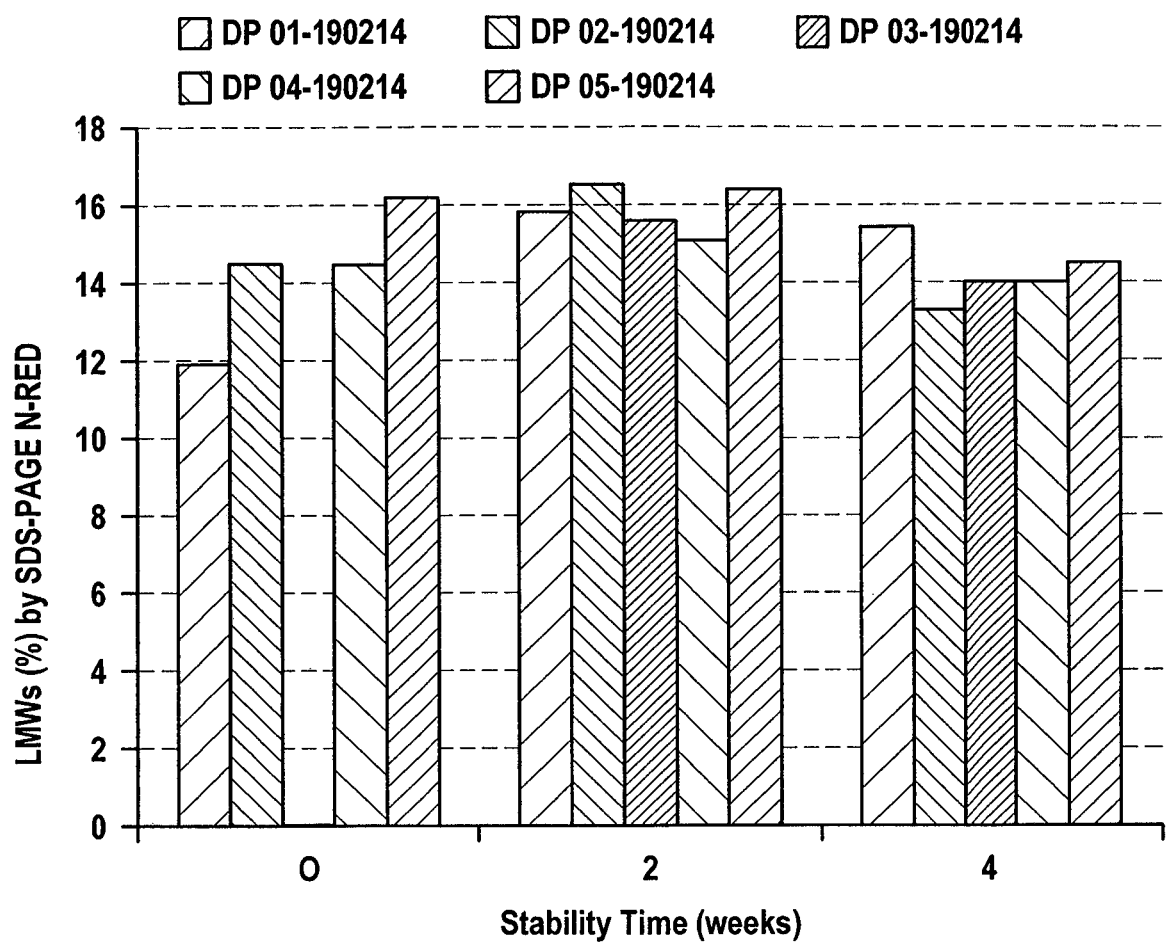
Figure 24:
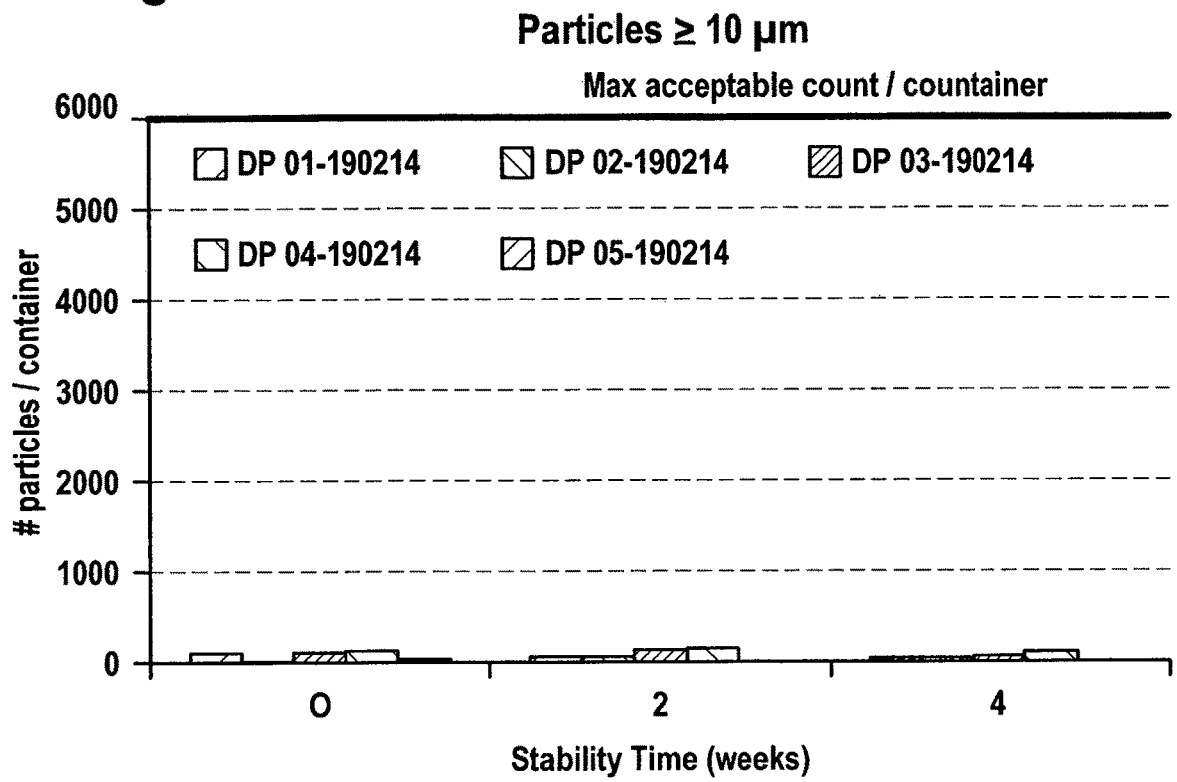
Figure 25:
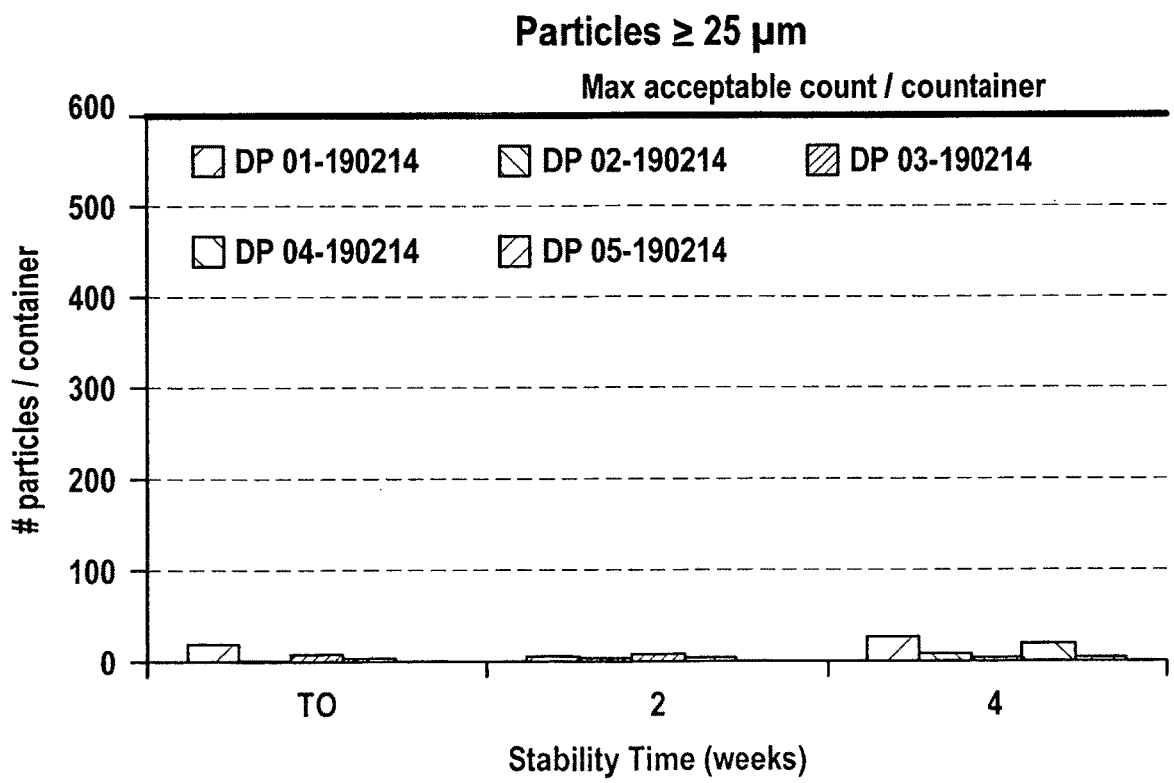
Figure 26:
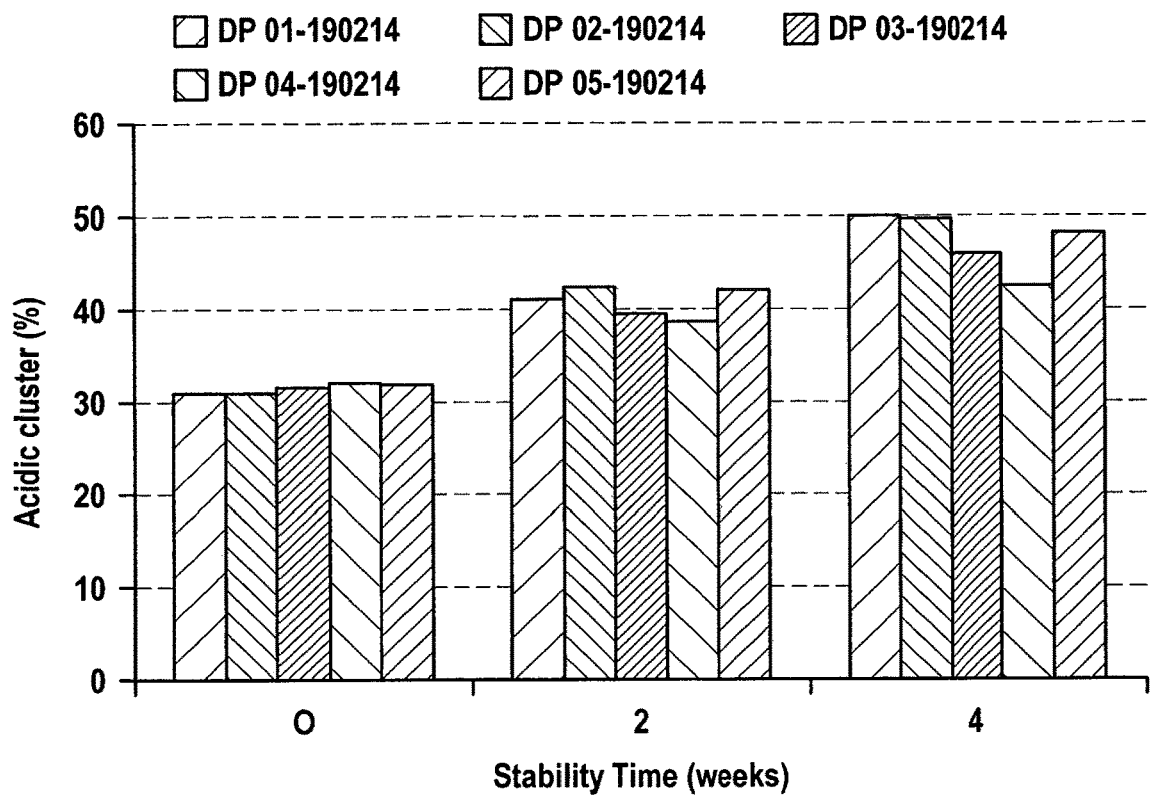
Figure 27:
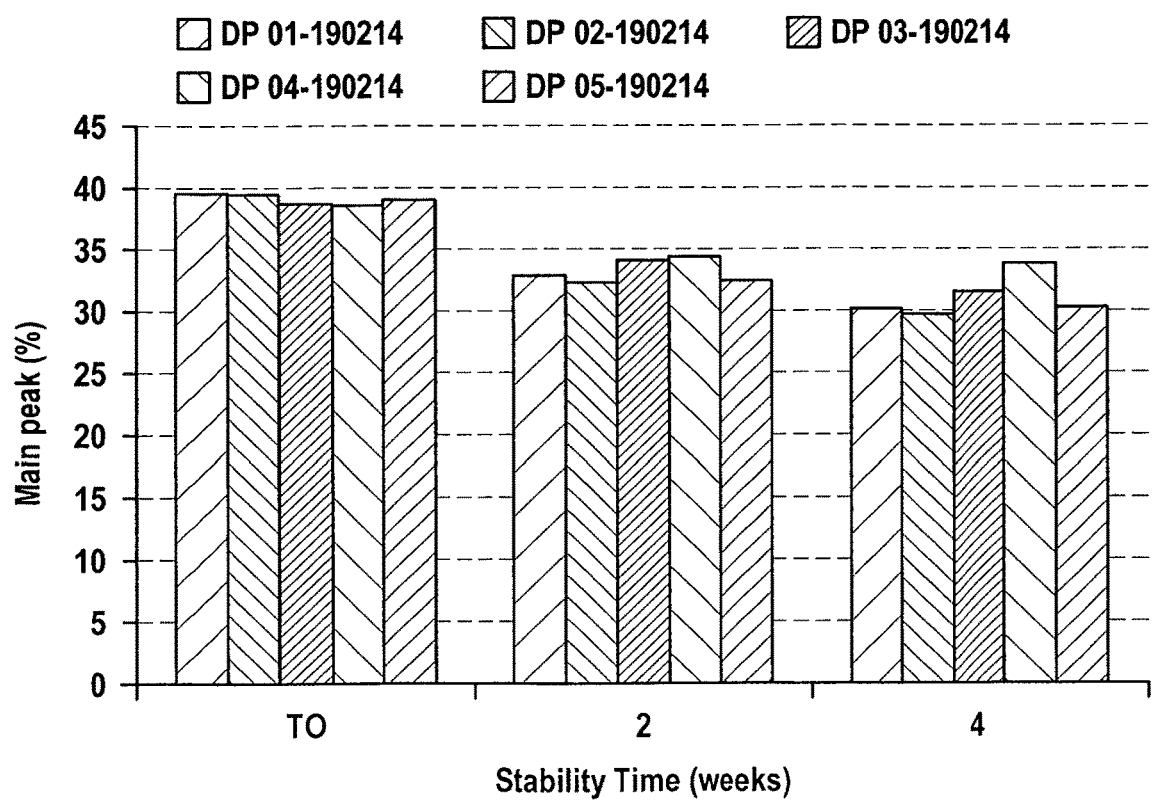
Figure 28:
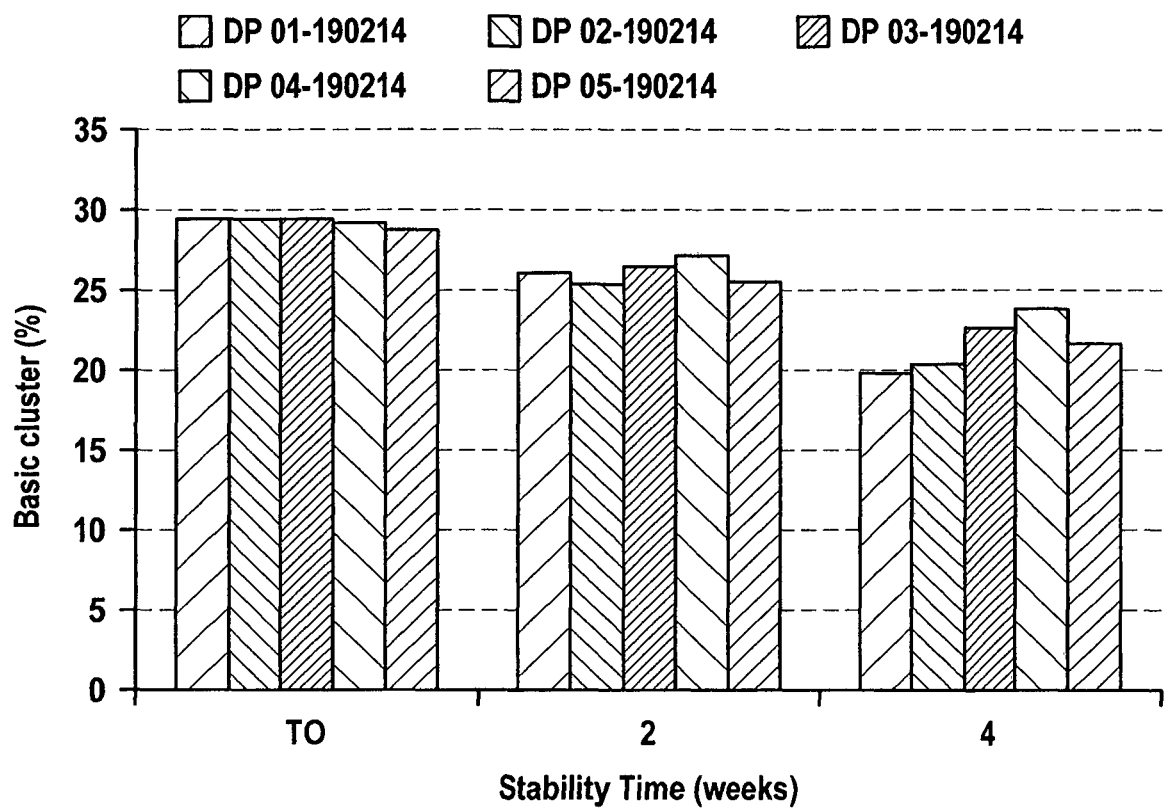

FIG. 1a: Heavy chain sequence of Avelumab (SEQ ID NO:1)
FIG. 1b: Heavy chain sequence of Avelumab, lacking the C-terminal K (SEQ ID NO:2)
FIG. 2: Light chain sequence of Avelumab (SEQ ID NO:3)
FIG. 3: Secondary structure of Avelumab
FIG. 4: 2AB HILIC-UPLC Chromatogram of Avelumab Glycans
FIG. 5: Numbering of the peaks of FIG. 4
FIG. 6: Total aggregates by SE-HPLC of DoE2 formulations (40° C.)
FIG. 7: Total aggregates by SE-HPLC of DoE2 formulations (25° C.)
FIG. 8: Fragments by Bioanalyzer of DoE2 formulations (40° C.)
FIG. 9: Fragments by Bioanalyzer of DoE2 formulations (25° C.)
FIG. 10: Acidic cluster and main peak abundance of DoE2 (25° C.)
FIG. 11: Long Term Stability LMWs (%) at 2-8° C.
FIG. 12: Long Term Stability Sub-visible particles ≥10 μm at 2-8° C.
FIG. 13: Long Term Stability Sub-visible particles ≥25 μm at 2-8° C.
FIG. 14: Long Term Stability Acidic cluster (%) at 2-8° C.
FIG. 15: Long Term Stability Main peak (%) at 2-8° C.
FIG. 16: Long Term Stability Basic cluster (%) at 2-8° C.
FIG. 17: Long Term Stability LMWs (%) at 25° C.
FIG. 18: Long Term Stability Sub-visible particles ≥10 μm at 25° C.
FIG. 19: Long Term Stability Sub-visible particles ≥25 μm at 25° C.
FIG. 20: Long Term Stability Acidic cluster (%) at 25° C.
FIG. 21: Long Term Stability Main peak (%) at 25° C.
FIG. 22: Long Term Stability Basic cluster (%) at 25° C.
FIG. 23: Long Term Stability LMWs (%) at 40° C.
FIG. 24: Long Term Stability Sub-visible particles ≥10 μm at 40° C.
FIG. 25: Long Term Stability Sub-visible particles ≥25 μm at 40° C.
FIG. 26: Long Term Stability Acidic cluster (%) at 40° C.
FIG. 27: Long Term Stability Main peak (%) at 40° C.
FIG. 28: Long Term Stability Basic cluster (%) at 40° C.
FIGS. 29A-29B: Peak identification of 2AB HILIC-UPLC chromatogram. Man: mannose, Fuc: fucose, Gal: galactose, GalNAc: N-Acetylgalactosamine, NANA: sialic acid, NGNA: N-glycolylneuraminic acid

DEFINITIONS

Unless otherwise stated, the following terms used in the specification and claims have the following meanings set out below.

References herein to "Avelumab" include the anti-PD-L1 antibody of the IgG1 type as defined in WO2013079174 by its amino acid sequence, and as defined in the present patent application by its amino acid sequence and by its post-translational modifications. References herein to "Avelumab" may include biosimilars which, for instance, may share at least 75%, suitably at least 80%, suitably at least 85%, suitably at least 90%, suitably at least 95%, suitably at least 96%, suitably at least 97%, suitably at least 98% or most suitably at least 99% amino acid sequence identity with the amino acid sequences disclosed in WO2013079174. Alternatively or additionally, references herein to "Avelumab" may include biosimilars which differ in the post-translational modifications, especially in the glycosylation pattern, herein disclosed.

The term "biosimilar" (also known as follow-on biologics) is well known in the art, and the skilled person would readily appreciate when a drug substance would be considered a biosimilar of Avelumab. The term "biosimilar" is generally used to describe subsequent versions (generally from a different source) of "innovator biopharmaceutical products" ("biologics" whose drug substance is made by a living organism or derived from a living organism or through recombinant DNA or controlled gene expression methodologies) that have been previously officially granted marketing authorisation. Since biologics have a high degree of molecular complexity, and are generally sensitive to changes in manufacturing processes (e.g. if different cell lines are used in their production), and since subsequent follow-on manufacturers generally do not have access to the originator's molecular clone, cell bank, know-how regarding the fermentation and purification process, nor to the active drug substance itself (only the innovator's commercialized drug product), any "biosimilar" is unlikely to be exactly the same as the innovator drug product.

Herein, the term "buffer" or "buffer solution" refers to a generally aqueous solution comprising a mixture of an acid (usually a weak acid, e.g. acetic acid, citric acid, imidazolium form of histidine) and its conjugate base (e.g. an acetate or citrate salt, for example, sodium acetate, sodium citrate, or histidine) or alternatively a mixture of a base (usually a weak base, e.g. histidine) and its conjugate acid (e.g. protonated histidine salt). The pH of a "buffer solution" will change very only slightly upon addition of a small quantity of strong acid or base due to the "buffering effect" imparted by the "buffering agent".

Herein, a "buffer system" comprises one or more buffering agent(s) and/or an acid/base conjugate(s) thereof, and more suitably comprises one or more buffering agent(s) and an acid/base conjugate(s) thereof, and most suitably comprises one buffering agent only and an acid/base conjugate thereof. Unless stated otherwise, any concentrations stipulated herein in relation to a "buffer system" (i.e. a buffer concentration) suitably refers to the combined concentration of the buffering agent(s) and/or acid/base conjugate(s)

thereof. In other words, concentrations stipulated herein in relation to a "buffer system" suitably refer to the combined concentration of all the relevant buffering species (i.e. the species in dynamic equilibrium with one another, e.g. citrate/citric acid). As such, a given concentration of a histidine buffer system generally relates to the combined concentration of histidine and the imidazolium form of histidine. However, in the case of histidine, such concentrations are usually straightforward to calculate by reference to the input quantities of histidine or a salt thereof. The overall pH of the composition comprising the relevant buffer system is generally a reflection of the equilibrium concentration of each of the relevant buffering species (i.e. the balance of buffering agent(s) to acid/base conjugate(s) thereof).

Herein, the term "buffering agent" refers to an acid or base component (usually a weak acid or weak base) of a buffer or buffer solution. A buffering agent helps maintain the pH of a given solution at or near to a pre-determined value, and the buffering agents are generally chosen to complement the pre-determined value. A buffering agent is suitably a single compound which gives rise to a desired buffering effect, especially when said buffering agent is mixed with (and suitably capable of proton exchange with) an appropriate amount (depending on the pre-determined pH desired) of its corresponding "acid/base conjugate", or if the required amount of its corresponding "acid/base conjugate" is formed in situ—this may be achieved by adding strong acid or base until the required pH is reached. For example in the sodium acetate buffer system, it is possible to start out with a solution of sodium acetate (basic) which is then acidified with, e.g., hydrochloric acid, or to a solution of acetic acid (acidic), sodium hydroxide or sodium acetate is added until the desired pH is reached.

Generally, a "stabiliser" refers to a component which facilitates maintenance of the structural integrity of the biopharmaceutical drug, particularly during freezing and/or lyophilization and/or storage (especially when exposed to stress). This stabilising effect may arise for a variety of reasons, though typically such stabilisers may act as osmolytes which mitigate against protein denaturation. As used herein, stabilisers are amino acids (i.e. free amino acids not part of a peptide or protein—e.g. glycine, arginine, histidine, aspartic acid, lysine) and sugar stabilisers, such as a sugar polyol (e.g. mannitol, sorbitol), and/or a disaccharide (e.g. trehalose, sucrose, maltose, lactose).

Agents used as buffering agents, antioxidants or surfactants according to the invention, are excluded from the meaning of the term "stabilisers" as used herein, even if they may exhibit, i.a. stabilising activity.

Herein, the term "surfactant" refers to a surface-active agent, preferably a nonionic surfactant. Examples of surfactants used herein include polysorbate (for example, polysorbate 20 (polyoxyethylene (20) sorbitan monolaurate) also known under the tradename Tween 20); poloxamer (e.g. poloxamer 188, a non-ionic triblock copolymers composed of a central hydrophobic chain of polyoxypropylene (poly (propylene oxide)) flanked by two hydrophilic chains of polyoxyethylene (poly(ethylene oxide)), also known under the tradename Lutrol F 68).

Herein, the term "stable" generally refers to the physical stability and/or chemical stability and/or biological stability of a component, typically an active or composition thereof, during preservation/storage.

Agents used as buffering agents, antioxidants or stabilisers according to the invention, are excluded from the meaning of the term "surfactants" as used herein, even if they may exhibit, i.a. surfactant activity.

Herein, the term "antioxidant" refers to an agent capable of preventing or decreasing oxidation of the biopharmaceutical drug to be stabilized in the formulation. Antioxidants include radical scavengers (e.g. ascorbic acid, BHT, sodium sulfite, p-amino benzoic acid, glutathione or propyl gallate), chelating agents (e.g. EDTA or citric acid) or chain terminators (e.g. methionine or N-acetyl cysteine).

Agents used as buffering agents, stabilisers or surfactants according to the invention, are excluded from the meaning of the term "antioxidants" as used herein, even if they may exhibit, i.a. antioxidative activity.

A "diluent" is an agent that constitutes the balance of ingredients in any liquid pharmaceutical composition, for instance so that the weight percentages total 100%. Herein, the liquid pharmaceutical composition is an aqueous pharmaceutical composition, so that a "diluent" as used herein is water, preferably water for injection (WFI).

Herein, the term "particle size" or "pore size" refers respectively to the length of the longest dimension of a given particle or pore. Both sizes may be measured using a laser particle size analyser and/or electron microscopes (e.g. tunneling electron microscope, TEM, or scanning electron microscope, SEM). The particle count (for any given size) can be obtained using the protocols and equipment outlined in the Examples, which relates to the particle count of sub-visible particles.

Herein, the term "about" refers to the usual error range for the respective value readily known to the skilled person in this technical field. Reference to "about" a value or parameter herein includes (and describes) embodiments that are directed to that value or parameter per se. In case of doubt, or should there be no art recognized common understanding regarding the error range for a certain value or parameter, "about" means ±5% of this value or parameter.

Herein, the term "percent share" in connection with glycan species refers directly to the number of different species. For example the term "said FA2G1 has a share of 25%-41% of all glycan species" means that in 50 antibody molecules analysed, having 100 heavy chains, 25-41 of the heavy chains will exhibit the FA2G1 glycosylation pattern.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

Aqueous Anti-PD-L1 Antibody Formulation

In a first aspect, the invention provides a novel aqueous pharmaceutical antibody formulation, comprising:

(i) Avelumab in a concentration of 1 mg/mL to 30 mg/mL as the antibody;

(ii) acetate or histidine in a concentration of 5 mM to 15 mM as the buffering agent;

(iii) D-mannitol or trehalose in a concentration of 240 mM to 320 mM, or a combination of arginine HCl in a concentration of 50 to 150 mM and glutamic acid in a concentration of 25 mM to 75 mM as a stabiliser;

(iv) Poloxamer 188 or Polysorbate 20 in a concentration of 0.25 mg/mL to 0.75 mg/mL, as surfactant, or no surfactant;

wherein the formulation does not comprise methionine, and further wherein the formulation has a pH of 5.0 to 6.0, preferably, 5.0 to 5.6.

In a preferred embodiment the formulation does not comprise any antioxidant.

In an embodiment the concentration of Avelumab in the said formulation is about 10 mg/mL to about 20 mg/mL.

In another embodiment the concentration of acetate or histidine in the said formulation is about 10 mM.

In yet another embodiment the concentration of D-mannitol or trehalose in the said formulation is about 280 mM, or for the combination of arginine HCl and glutamic acid, the concentration of arginine HCl is about 150 mM and the concentration of glutamic acid is about 50 mM.

In yet another embodiment the concentration of Poloxamer 188 or Polysorbate 20 in the said formulation is about 0.5 mg/mL.

In yet another embodiment the pH of the said formulation is 5.2 (±0.1) to 5.5 (±0.1).

In a preferred embodiment the said formulation comprises acetate in a concentration of about 10 mM, and does not comprise any other buffering agent.

In another preferred embodiment the said formulation comprises D-mannitol or trehalose in a concentration of about 280 mM, and does not comprise any other stabiliser.

In yet another preferred embodiment the said formulation comprises Polysorbate 20 or Poloxamer 188 in a concentration of about 0.5 mg/mL, and does not comprise any other surfactant.

In an embodiment the said formulation comprises:
(i) Avelumab in a concentration of about 10 mg/mL as the antibody;
(ii) acetate in a concentration of about 10 mM as the buffering agent;
(iii) D-mannitol or trehalose in a concentration of about 280 mM as a stabiliser;
(iv) Polysorbate 20 or Poloxamer 188 in a concentration of about 0.5 mg/mL as surfactant;
and does not comprise methionine, and has a pH of about 5.5.

In a preferred embodiment the said formulation comprises:
(i) Avelumab in a concentration of 10 mg/mL;
(ii) acetate in a concentration of 10 mM;
(iii) D-mannitol or trehalose in a concentration of 280 mM;
(iv) Polysorbate 20 or Poloxamer 188 in a concentration of 0.5 mg/mL;
and has a pH of 5.5 (±0.1).

In a preferred embodiment the said formulation consists of:
(i) Avelumab in a concentration of 10 mg/mL;
(ii) sodium acetate trihydrate in a concentration of 10 mM;
(iii) D-mannitol or trehalose in a concentration of 280 mM;
(iv) Polysorbate 20 or Poloxamer 188 in a concentration of 0.5 mg/mL;
(v) HCl to adjust the pH;
(vi) water (for injection) as the solvent;
and has a pH of 5.5 (±0.1).

In a preferred embodiment the said formulation consists of:
(i) Avelumab in a concentration of 10 mg/mL;
(ii) sodium acetate trihydrate in a concentration of 10 mM;
(iii) trehalose dihydrate in a concentration of 280 mM;
(iv) Polysorbate 20 in a concentration of 0.5 mg/mL;
(v) HCl to adjust the pH;
(vi) water (for injection) as the diluent;
and has a pH of 5.5 (±0.1).

In a more preferred embodiment the said formulation consists of:
(i) Avelumab in a concentration of 10 mg/mL;
(ii) sodium acetate trihydrate in a concentration of 10 mM;
(iii) D-mannitol in a concentration of 280 mM;
(iv) Polysorbate 20 in a concentration of 0.5 mg/mL;
(v) HCl to adjust the pH;
(vi) water (for injection) as the diluent;
and has a pH of 5.5 (±0.1).

In another embodiment the said formulation comprises:
(i) Avelumab in a concentration of about 20 mg/mL as the antibody;
(ii) acetate in a concentration of about 10 mM as the buffering agent;
(iii) D-mannitol or trehalose in a concentration of about 280 mM as a stabiliser;
(iv) Polysorbate 20 or Poloxamer 188 in a concentration of about 0.5 mg/mL as surfactant;
and does not comprise methionine, and has a pH of 5.2 (±0.1).

In a preferred embodiment the said formulation comprises:
(i) Avelumab in a concentration of 20 mg/mL;
(ii) acetate in a concentration of 10 mM;
(iii) D-mannitol or trehalose in a concentration of 280 mM;
(iv) Polysorbate 20 or Poloxamer 188 in a concentration of 0.5 mg/mL;
and has a pH of 5.5 (±0.1).

In a preferred embodiment the said formulation comprises:
(i) Avelumab in a concentration of 20 mg/mL;
(ii) acetic acid in a concentration of 10 mM;
(iii) D-mannitol or trehalose dihydrate in a concentration of 280 mM;
(iv) Polysorbate 20 or Poloxamer 188 in a concentration of 0.5 mg/mL;
(v) sodium acetate to adjust the pH;
(vi) water (for injection) as the diluent;
and has a pH of 5.2 (±0.1).

In a more preferred embodiment the said formulation consists of:
(i) Avelumab in a concentration of 20 mg/mL;
(ii) acetic acid in a concentration of 10 mM;
(iii) D-mannitol in a concentration of 280 mM;
(iv) Polysorbate 20 in a concentration of 0.5 mg/mL;
(v) sodium acetate to adjust the pH;
(vi) water (for injection) as the diluent;
and has a pH of 5.2 (±0.1).

In a more preferred embodiment the said formulation consists of:
(i) Avelumab in a concentration of 20 mg/mL;
(ii) acetic acid in a concentration of 10 mM;
(iii) trehalose dihydrate in a concentration of 280 mM;
(iv) Polysorbate 20 in a concentration of 0.5 mg/mL;
(v) sodium acetate to adjust the pH;
(vi) water (for injection) as the diluent;
and has a pH of 5.2 (±0.1).

In a more preferred embodiment the said formulation consists of:
(i) Avelumab in a concentration of 20 mg/mL;
(ii) acetic acid in a concentration of 10 mM;
(iii) D-mannitol in a concentration of 280 mM;
(iv) Poloxamer 188 in a concentration of 0.5 mg/mL;
(v) sodium acetate to adjust the pH;
(vi) water (for injection) as the diluent;
and has a pH of 5.2 (±0.1).

In a more preferred embodiment the said formulation consists of:
(i) Avelumab in a concentration of 20 mg/mL;
(ii) acetic acid in a concentration of 10 mM;
(iii) trehalose dihydrate in a concentration of 280 mM;
(iv) Poloxamer 188 in a concentration of 0.5 mg/mL;
(v) sodium acetate to adjust the pH;
(vi) water (for injection) as the diluent;
and has a pH of 5.2 (±0.1).

In a preferred embodiment, the said formulation consists of:
(i) Avelumab in a concentration of 20 mg/mL;
(ii) acetic acid in a concentration of 10 mM (0.6 mg/mL);
(iii) D-mannitol in a concentration of 280 mM (51 mg/mL);
(iv) Polysorbate 20 in a concentration of 0.5 mg/mL;
(v) sodium hydroxide in a concentration of 7.5 mM (0.3 mg/mL);
(vi) water (for injection) as the diluent;
and has a pH of 5.0 to 5.6, preferably 5.2 (±0.1).

In a preferred embodiment, the latter formulation is made by combining:
(i) 20 mg/mL of Avelumab;
(ii) 0.6 mg/mL of glacial acetic acid;
(iii) 51 mg/mL of D-mannitol;
(iv) 0.5 mg/mL of Polysorbate 20;
(v) 0.3 mg/mL of sodium hydroxide;
(vi) water (for injection) as the diluent;
to obtain the desired volume of the formulation.

In a further embodiment, the invention concerns an aqueous pharmaceutical antibody formulation, whose pH is adjusted with sodium hydroxide. Therefore, the formulation consists of Avelumab in a concentration of 20 mg/mL as the active ingredient; and glacial acetic acid, D-mannitol, Polysorbate 20, sodium hydroxide and water for injection as the excipients; wherein the formulation has a pH of 5.0 to 5.6, preferably 5.2 (±0.1).

In a preferred embodiment, the formulation has a osmolality between 270 and 330 mOsm/kg.

In an embodiment said Avelumab in the formulations as described above has the heavy chain sequence of either FIG. 1a (SEQ ID NO:1) or FIG. 1b (SEQ ID NO:2), the light chain sequence of FIG. 2 (SEQ ID NO:3), and carries a glycosylation on Asn300 comprising FA2 and FA2G1 as the main glycan species, having a joint share of >70% of all glycan species.

In a preferred embodiment, in the Avelumab glycosylation the said FA2 has a share of 44%-54% and said FA2G1 has a share of 25%-41% of all glycan species.

In a preferred embodiment, in the Avelumab glycosylation the said FA2 has a share of 47%-52% and said FA2G1 has a share of 29%-37% of all glycan species.

In a preferred embodiment, in the Avelumab glycosylation the said FA2 has a share of about 49% and said FA2G1 has a share of about 30%-about 35% of all glycan species.

In a preferred embodiment the Avelumab glycosylation further comprises as minor glycan species A2 with a share of <5%, A2G1 with a share of <5%, A2G2 with a share of <5% and FA2G2 with a share of <7% of all glycan species.

In a preferred embodiment, in the Avelumab glycosylation said A2 has a share of 3%-5%, said A2G1 has a share of <4%, said A2G2 has a share of <3% and said FA2G2 has a share of 5%-6% of all glycan species.

In a preferred embodiment, in the Avelumab glycosylation said A2 has a share of about 3.5%-about 4.5%, said A2G1 has a share of about 0.5%-about 3.5%, said A2G2 has a share of <2.5% and said FA2G2 has a share of about 5.5% of all glycan species.

In an embodiment the said Avelumab in the formulation as described above has the heavy chain sequence of FIG. 1b (SEQ ID NO:2).

In an embodiment the Avelumab formulation as described above is for intravenous (IV) administration.

Drug-Delivery Device

In a second aspect the present invention provides a drug delivery device comprising a liquid pharmaceutical composition as defined herein. Suitably the drug delivery device comprises a chamber within which the pharmaceutical composition resides. Suitably the drug delivery device is sterile.

The drug delivery device may a vial, ampoule, syringe, injection pen (e.g. essentially incorporating a syringe), or i.v. (intravenous) bag.

The aqueous pharmaceutical formulations are parenterally administered, preferably via sub-cutaneous injection, intramuscular injection, i.v. injection or i.v. infusion. The most preferred way of administration is i.v. infusion.

In a preferred embodiment, the drug delivery device is a vial containing the formulation as described above.

In a more preferred embodiment the said vial contains 200 mg avelumab in 10 mL of solution for a concentration of 20 mg/mL.

In an even more preferred embodiment the vial is a glass vial.

Medical Treatment

In a third aspect, the invention provides a method of treating cancer comprising administering the formulation as described above to a patient, In an embodiment the cancer to be treated is selected from non-small cell lung cancer, urothelial carcinoma, bladder cancer, mesothelioma, Merkel cell carcinoma, gastric or gastroesophageal junction cancer, ovarian cancer, breast cancer, thymoma, adenocarcinoma of the stomach, adrenocortical carcinoma, head and neck squamous cell carcinoma, renal cell carcinoma, melanoma, and/or classical Hodgkin's lymphoma.

Abbreviations

ANOVA Analysis of variance
CD Cicular Dichroism
CE Capillary Electrophoresis
DoE Design of Experiments
DP Drug Product
DS Drug Substance
DSF Differential Scanning Fluorimetry
DTT Dithiothreitol
ESI Electrospray Ionization
HILIC Hydrophilic Interaction Liquid Chromatography
HMWs Higher Molecular Weights
HPLC High Performance Liquid Chromatography
iCE Capillary Isoelectric Focusing
LC Liquid Chromatography
LMWs Lower Molecular Weights
MALDI Matrix-Assisted Laser Desorption Ionization MS Mass Spectromety
NTU Nephelometry Turbidity Units
OD Optical density
PBS Poly Buffer Saline
PES Polyethersulfone
PVDF Polyvinylidene Fluoride
SDS-PAGE Sodium Dodecyl Sulphate-PolyAcrylamide Gel Electrophoresis
SE Size Exclusion
TOF Time of Flight
UPLC Ultra Performance Liquid Chromatography
RH Residual Humidity
UV Ultraviolet

EXAMPLES

Methods Used to Determine Stability

In order to assess the stability of the antibody formulations tested, and select the best candidates, thermal stress, mechanical stress, light exposure, osmolality, turbidity, protein content, total aggregates, fragmentation, pH, isoforms, circular dichroism, sub-visible particles and biological activity were determined as stability parameters according to the following protocols:

Thermal Stress:

At 40° C.: the samples in the original vial container were incubated in a thermostatic cabinet at a temperature of 40° C.±2° C. (RH 75%±5%) and withdrawn at pre-determined time points.

At 25° C.: the samples in the original vial container were incubated in a thermostatic cabinet at a temperature of 25° C.±2° C. (RH 60%±5%) and withdrawn at pre-determined time points.

Mechanical Stress:

The samples in the original vial container were placed on an orbital shaker maintained at 300 rpm for up to 24 hours (room temperature).

Light Exposure:

The samples in the original vial container were exposed to a light source for 7 hours adjusting the irradiance level in the Suntest machine to 765 W/m$^2$ (radiation wavelength between 320 nm and 800 nm).

Osmolality:

Normal human plasma has an osmolality of about 280 mOSm/kg (Medical Physiology-Principles for Clinical Medicine. Edited by Rodney A. Rhoades PhD, David R. Bell PhD). In general, solutions with osmolality close to 300 mOsm/kg are to be targeted when developing parenteral formulations. Acceptable ranges (as per product specifications) are 250-400 mOsm/kg.

Here, osmolality was determined by a cryoscopic method determining the freezing point depression of water solutions after addition of solutes. Amount of solutes, and hence the observed osmolality value is proportional to the observed freezing point depression of the compounded solution.

Turbidity:

The turbidity of the solutions were determined with a nephelometer with the capability to measure scattered or attenuated light (Hach Lange Model 2100AN). About 3 mL of solution in reduced volume cuvettes were illuminated by an 870±30 nm light emitting diode (LED) assembly. A detector monitors the scattered light and provided the turbidity (NTU) of the solution by comparison with a series of standards of known turbidity.

Protein Content:

Protein content was determined via the optical density of solutions (diluted to ~0.5 mg/mL protein concentration with relevant buffer) at 280 nm and 320 nm in 1 cm path length quartz cuvettes. Assuming a molar extinction coefficient of 1.46 cm$^2$/mg, protein concentration was obtained by applying the formula: (A280−A320)/(1.46 cm$^2$/mg×1 cm).

Total Aggregates:

The amount of aggregates was determined by the SE-HPLC method. A sample volume of 20 µL (sample diluted to about 0.5 mL with PBS) was injected in a TSK gel Super SW3000 4.6 mm×30 cm (cod. 18675) kept at a temperature of 22±5° C. at a flow rate of 0.35 mL/min (mobile phase was 50 mM sodium phosphate+0.4 sodium perchlorate at pH 6.3±0.1). UV detection at 214 nm.

Fragmentation:

Low molecular species (or fragments) were determined by Bioanalyzer. Samples are analyzed at a concentration ranging between 1.25-3.75 mg/mL (dilutions made with purified water). 3 µL of each diluted sample were merged with 2 µL of the corresponding sample buffer (with the addition of DTT when tests were conducted under reducing conditions) and 1 µL of a 60 mM maleimide solution. The samples were heated for 5 minutes at 70° C., then 84 µL of purified water were added and the solutions vortexed and spun down. 64 were loaded onto the chip (0.25-0.75 µg of protein). The chip was placed into the Agilent 2100 Bioanalyzer and the analysis started within the following five minutes.

Isoforms:

Isoforms distribution was determined by iCE. An Fc coated capillary cartridge (100 mm internal diameter and 50 mm length) was used. The separation is conducted using a 100 mM NaOH solution in 0.1% methylcellulose as a cathodic solution and a 80 mM o-phosphoric acid in 0.1% methylcellulose as an anodic solution. The samples were prepared starting from 80 µL of master mix solution (obtained mixing 700 µL of 0.1% methylcellulose, 104 of Pharmalyte 5-8, 70 µL of Pharmalyte 8-10.5, 10 µL of a 7.65 pI marker and 10 µL of a 9.77 pI marker), to which the suitable volume of washed Avelumab sample (corresponding to 200 µg of protein after washing to remove formulation components) was added. An amount of purified water corresponding to (120 µL—volume of washed Avelumab sample added at the previous step) is added. The separation is conducted at a detection wavelength of 280 nm setting pre-focusing and focusing times of 1 and 15 minutes respectively and pre-focusing and focusing voltages of 1500 V and 3000 V respectively. Samples were injected at a pressure of 1000 mBar.

pH: was determined by conventional potentiometry.

Circular Dichroism (CD):

Investigations on tertiary structure of Avelumab were carried out using a CD spectropolarimeter by Jasco (mod. J810) in the near UV range (320-250 nm). Samples were diluted to 1.5 mg/mL protein concentration with purified water and, once filled in 1 cm-path length quartz cuvettes, analyzed at room temperature, at a scanning speed of 20 nm/min, with a data pitch of 0.5 nm, integration time of 8 s and standard sensitivity.

Sub-Visible Particles:

Sub-visible particles were counted through the technique of light obscuration method using a Pamas SVSS-C particle counter. Samples were diluted 5-fold with purified water to obtain a final volume of at least 25 mL to be tested.

Biological Activity:

For the long term stability studies described in Example 5 biological activity was measured as an additional stability parameter.

The method used is based on the ability of Avelumab, absorbed on an ELISA plate, to bind in a dose-dependent manner its antigen PD-L1 present on the cell line HEK-293 (hPDL1, permanently transfected with PD-L1). Dosages used were 400, 200, 100, 50, 25, 12.5, 6.25 and 3.12 ng/mL. From the data obtained $EC_{50}$ values were calculated. The biological activity (potency) of the samples is expressed as the percentage of bioactivity of the sample against the standard and is calculated as follows: Potency (sample) [%]=($EC_{50}$ (sample)/$EC_{50}$ (standard))*100.7.

Methods of Manufacturing

The present invention also provides a method of manufacturing an aqueous pharmaceutical formulation as defined herein. The method suitably comprises mixing together, in any particular order deemed appropriate, any relevant components required to form the aqueous pharmaceutical formulation. The skilled person may refer to the examples or techniques well known in the art for forming aqueous pharmaceutical formulations (especially those for injection via syringe, or i.v. infusion).

The method may involve first preparing a pre-mixture (or pre-solution) of some or all components (optionally with some or all of the diluent) excluding Avelumab, and Avelumab may then itself (optionally with or pre-dissolved in some of the diluent) be mixed with the pre-mixture (or pre-solution) to afford the aqueous pharmaceutical formulation, or a composition to which final components are then added to furnish the final aqueous pharmaceutical formulation. Preferably, the method involves forming a buffer system, suitably a buffer system comprising a buffering agent as defined herein. The buffer system is suitably formed in a pre-mixture prior to the addition of Avelumab. The buffer system may be formed through simply mixing the buffering agent (supplied ready-made) with its acid/base conjugate (suitably in appropriate relative quantities to provide the desired pH—this can be determined by the skilled person either theoretically or experimentally). In the case of an acetate buffer system, this means e.g. mixing sodium acetate with HCl, or mixing acetic acid with NaOH or acetate. The pH of either the pre-mixture of final aqueous pharmaceutical formulation may be judiciously adjusted by adding the required quantity of base or acid, or a quantity of buffering agent or acid/base conjugate.

In certain embodiments, the buffering agent and/or buffer system is pre-formed as a separate mixture, and the buffer system is transferred to a precursor of the aqueous pharmaceutical formulation (comprising some or all components save for the buffering agent and/or buffer system, suitably comprising Avelumab and potentially only Avelumab) via buffer exchange (e.g. using diafiltration until the relevant concentrations or osmolality is reached). Additional excipients may be added thereafter if necessary in order to produce the final liquid pharmaceutical composition. The pH may be adjusted once or before all the components are present.

Any, some, or all components may be pre-dissolved or pre-mixed with a diluent prior to mixing with other components.

The final aqueous pharmaceutical formulation may be filtered, suitably to remove particulate matter. Suitably filtration is through filters sized at or below 1 μm, suitably at 0.22 μm. Suitably, filtration is through either PES filters or PVDF filters, suitably with 0.22 μm PES filters.

The person of skill in the art is well aware how an aqueous pharmaceutical formulation can be used to prepare an IV solution, so that the antibody drug substance can be administered intravenously.

The preparation of the IV solution typically consists of a certain amount of solution being withdrawn from saline bags (e.g. 0.9% or 0.45% saline) with a plastic syringe (PP) and a needle and replaced with aqueous pharmaceutical formulation. The amount of solution replaced will depend on the body weight of the patients.

Example 1—Structure of Avelumab 1.1 Primary Structure

Avelumab is an IgG with two heavy and two light chain molecules. The amino acid sequences of the two chains are shown in FIGS. 1a (SEQ ID NO:1)/1b (SEQ ID NO:2) and 2 (SEQ ID NO:3), respectively.

1.2 Secondary Structure

LC-MS and MS/MS methods were used to confirm the intact chains of the molecule and the presence of post-translational modifications to the proteins. The secondary structure of the Avelumab molecule subunits are shown in FIG. 3.

As confirmed by UPLC-Q-TOF mass spectrometry of peptides obtained by trypsin digestion, the disulfide bonds Cys21-Cys96, Cys21-Cys90, Cys147-Cys203, Cys138-Cys197, Cys215-Cys223, Cys229-Cys229, Cys232-Cys232, Cys264-Cys324 and Cys370-Cys428 are forming the nine typical IgG bonding pattern.

1.3 Glycosylation

The molecule contains one N-glycosylation site on Asn300 of the heavy chain. As determined by peptide mapping, the main structure identified by MALDI-TOF was a complex, biantennary type core fucosylated oligosaccharide with zero (G0F), one (G1F), or two galactose (G2F) residues. The main species are G0F and G1F.

Figure 4:
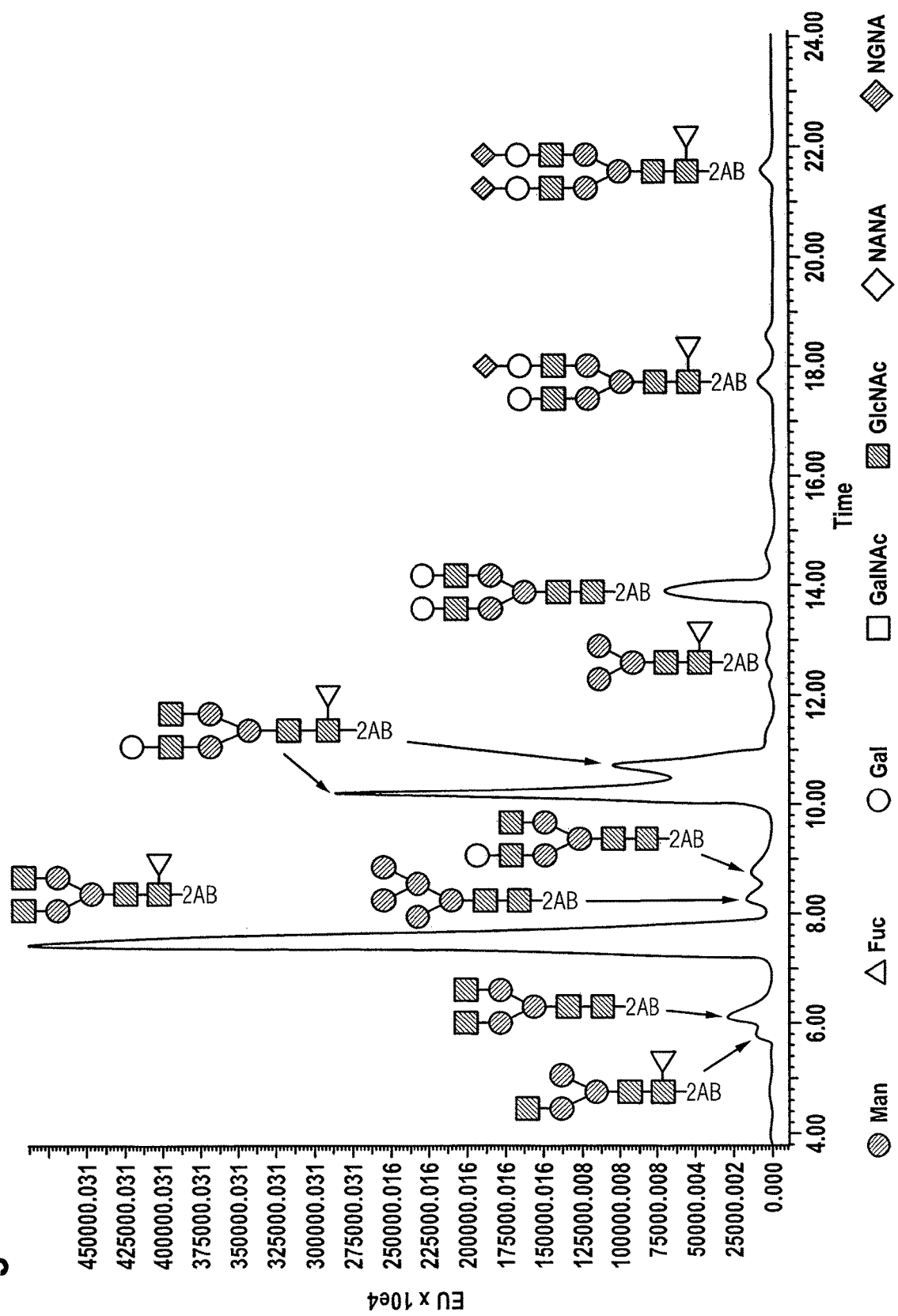
Figure 5:
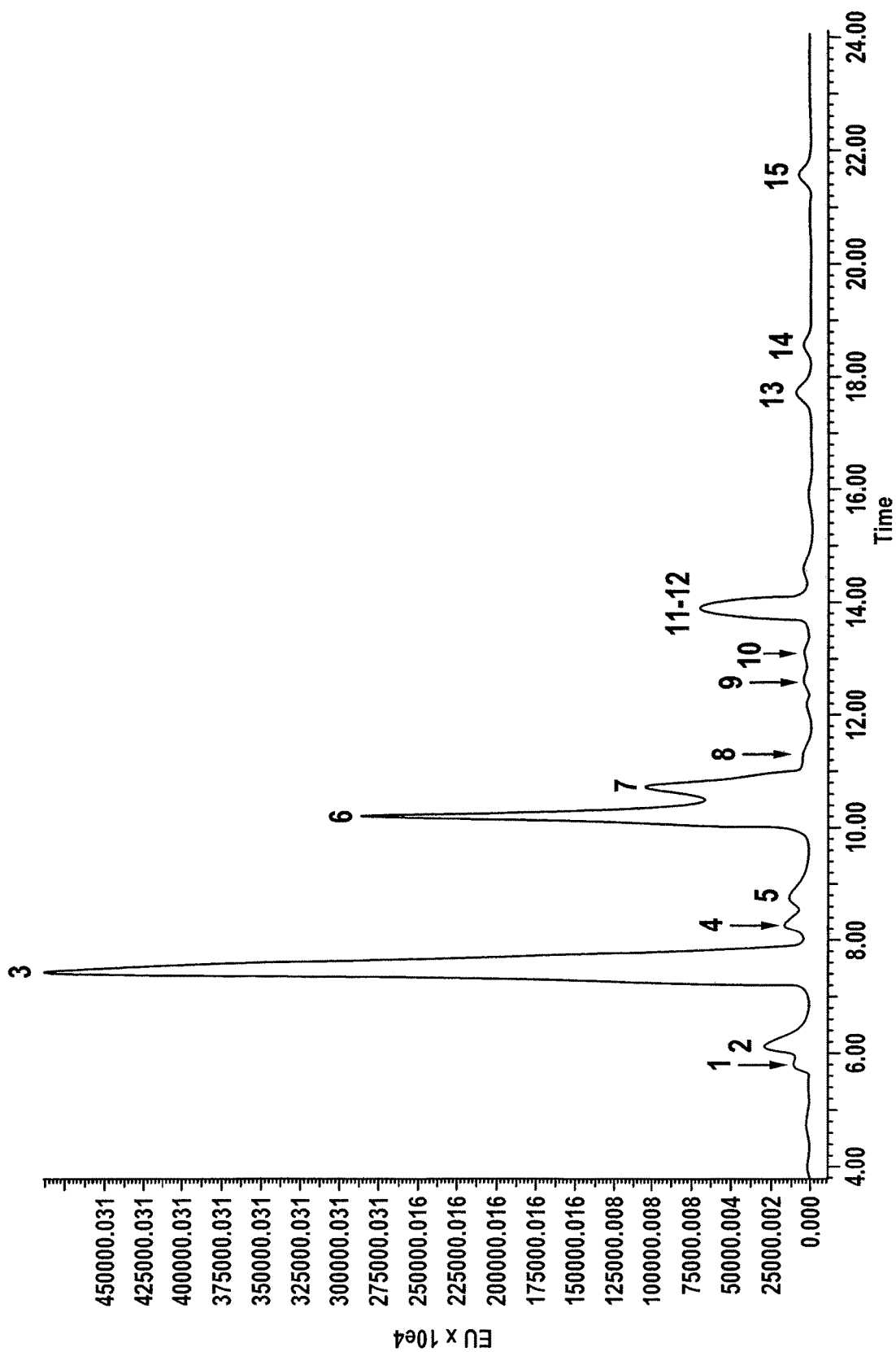

Avelumab glycans fluorescence labeled by 2-aminobenzamide have been analysed by HILIC-UPLC-ESI-Q-TOF. FIG. 4 shows the UPLC profile of the glycan species found. FIGS. 29A-29B show the peak identification of the 2AB HILIC UPLC chromatogram.

The glycan nomenclature used follows the Oxford Notation as proposed by Harvey et al. (Proteomics 2009, 9, 3796-3801). In species containing fucose (FA2, FA2G1, FA2G2), the Fuc-GlcNAc connectivity is α1-6. In species having a terminal GlcNAc, the GlcNAc-Man connectivity is α1-2. In species containing galactose, the Gal-GlcNAc connectivity is β1-4.

The reported chromatographic profile has been integrated and yielded the Glycan Species Distribution of Avelumab as shown in Table 1a.

TABLE 1a

| A2 | FA2 | A2G1 | FA2G1 | A2G2 | FA2G2 | M5** |
|---|---|---|---|---|---|---|
| 3.6 | 48.7 | 3.4 | 35.6 | 2.3 | 5.4 | 1.0 |

**Probably Mannose 5, coelution with biantennary mono-galactosylated species

The glycan mapping analysis confirmed the identification carried out by peptide mapping (that allowed to identify the two main glycan species), in addition secondary and minor species were also characterized by this method, specific for glycan analysis.

In another measurement the following Glycan Species Distribution was observed.

TABLE 1b

| A2 | FA2 | A2G1 | FA2G1 | A2G2 | FA2G2 |
|---|---|---|---|---|---|
| 4.0 | 50.2 | 1.0 | 30.0 | 0.1 | 5.6 |

Example 2—DoE1 Screening

A first Design of Experiment screening DoE1 at 10 mg/mL Avelumab assessed the impact of several factors such as varying buffer type/pH, excipients, surfactant type and relevant concentration. The study led to the selection of the optimal conditions which can maximize protein stability.

In DoE1 the following factors were taken into account for investigation:
- Buffer type and pH: acetate, citrate and histidine buffers to be evaluated in the pH range 5.0-6.0.
- Excipients: 3 different excipients were considered in order to give indications as to whether sugars/polyols or amino acids are to be preferred for compounding in the formula,
- Surfactant type and concentration: two alternative surfactants (Tween 20 and Poloxamer 188) to be evaluated at varying concentrations (0-1 mg/mL).

The study was conducted in DINER vials (Schott) at a protein concentration of 10 mg/mL with filling volumes of 8 mL (80 mg/vial).

Table 2 illustrates the selection of DoE1 formulas investigated.

DoE1 allowed a selection of suitable buffer/pH, excipient type and surfactant type to be made, that were used for the subsequent DoE2 study described in Example 3.

2.1 Manufacturing

The pre-formulated drug substance (DS) (10 (±1) mg/mL Avelumab, 1.36 mg/mL Sodium acetate trihydrate, 51 mg/mL D-Mannitol, 0.21 mg/mL L-Methionine, hydrochloric acid q.b. to pH 5.5) was buffer exchanged by tangential flow filtration (using Pellicon XL Biomax Cassettes with a 10 kDa cut-off) in the three buffers: 10 mM sodium acetate pH 5.0, 10 mM sodium citrate pH 5.0 and 10 mM histidine pH 5.75 until a three-fold volume exchange was achieved. At each step the DS solution was diluted 5-fold with relevant buffer. Final target protein concentration in the exchanged DS material was >10 mg/mL. The required excipients were then added to the relevant buffer-exchanged DS material, pH and final solution weight adjusted to the target so as to obtain the DP compositions listed in Table 2.

The sequence of addition of ingredients to the exchanged DS solutions was as follows: Add D-Mannitol or Trehalose dihydrate or Arginine HCl+Glutamic acid to the exchanged DS solution, stir until complete dissolution, add L-Methionine and stir until complete dissolution (only for Reference), add Poloxamer 188 or Polysorbate 20 (50 mg/mL stock solution), stir until complete dissolution, check pH and adjust to target with sodium hydroxide.

Drug product (DP) solutions were filled (8 mL) in DINER vials (Schott).

Visual inspection during the DS diafiltration process revealed that sodium citrate buffer caused generally higher

TABLE 2

DoE1 screening formulations

| ID | Avelumab (mg/mL) | pH | Buffer (10 mM) | Excipient | Surfactant | Surfactant concentration (mg/mL) |
|---|---|---|---|---|---|---|
| DoE1-1 | 10 | 5.00 | Acetate | Mannitol (51 mg/mL[1]) | Poloxamer 188 | 0.5 |
| DoE1-2 | 10 | 5.00 | Acetate | Trehalose dihydrate (106 mg/mL[1]) | Tween 20 | 0.5 |
| DoE1-3 | 10 | 5.00 | Citrate | Mannitol (51 mg/mL[1]) | Poloxamer 188 | 0.2 |
| DoE1-4 | 10 | 5.25 | Acetate | Trehalose dihydrate (106 mg/mL[1]) | Tween 20 | 0.2 |
| DoE1-5 | 10 | 5.25 | Acetate | Arginine HCl (21.1 mg/mL[2]) + Glutamic acid (7.4 mg/mL[3]) | Poloxamer 188 | 0.2 |
| DoE1-6 | 10 | 5.25 | Citrate | Arginine HCl (21.1 mg/mL[2]) + Glutamic acid (7.4 mg/mL[3]) | — | — |
| DoE1-7 | 10 | 5.25 | Citrate | Mannitol (51 mg/mL[1]) | Tween 20 | 0.2 |
| DoE1-8 | 10 | 5.50 | Acetate | Mannitol (51 mg/mL[1]) | Tween 20 | 0.5 |
| DoE1-9 | 10 | 5.50 | Acetate | Trehalose dihydrate (106 mg/mL[1]) | — | — |
| DoE1-10 | 10 | 5.50 | Citrate | Trehalose dihydrate (106 mg/mL[1]) | Poloxamer 188 | 1 |
| DoE1-11 | 10 | 5.50 | Citrate | Arginine HCl (21.1 mg/mL[2]) + Glutamic acid (7.4 mg/mL[3]) | Tween 20 | 0.2 |
| DoE1-12 | 10 | 5.75 | Citrate | Trehalose dihydrate (106 mg/mL) | Tween 20 | 1 |
| DoE1-13 | 10 | 5.75 | Citrate | Mannitol (51 mg/mL) | — | — |
| DoE1-14 | 10 | 5.75 | Histidine | Arginine HCl (21.1 mg/mL) + Glutamic acid (7.4 mg/mL) | Poloxamer 188 | 0.5 |
| DoE1-15 | 10 | 5.75 | Histidine | Mannitol (51 mg/mL) | Tween 20 | 1 |
| DoE1-16 | 10 | 6.00 | Citrate | Arginine HCl (21.1 mg/mL) + Glutamic acid (7.4 mg/mL) | Tween 20 | 1 |
| DoE1-17 | 10 | 6.00 | Citrate | Trehalose dihydrate (106 mg/mL) | Poloxamer 188 | 0.2 |
| DoE1-18 | 10 | 6.00 | Histidine | Arginine HCl (21.1 mg/mL) + Glutamic acid (7.4 mg/mL) | Poloxamer 188 | 1 |
| DoE1-19 | 10 | 6.00 | Histidine | Trehalose dihydrate (106 mg/mL) | Poloxamer 188 | 0.5 |
| Reference[4] | 10 | 5.50 | Acetate | Mannitol (51 mg/mL)/ L-Methionine (0.21 mg/mL) | Tween 20 | 0.5 |

[1] Corresponds to 280 mM
[2] Corresponds to 150 mM
[3] Corresponds to 50 mM
[4] Formulation disclosed in WO2013079174 opalescence, whilst remarkably clearer solutions were obtained when exchanges were made in sodium acetate and in histidine buffers.

In Table 3, the results of the experiments carried out to determine protein recovery, osmolality (Osmomat 030/D, Gonotec) and turbidity of the three DS materials upon buffer exchange are shown. Satisfactory protein recoveries (>89%) and final osmolality values (<61 mOsm/kg) were obtained. Turbidity analyses confirmed the higher opalescence of the DS exchanged in sodium citrate.

TABLE 3

Results of recovery (by OD), osmolality and turbidity experiments conducted on DS materials after buffer exchange.

| Buffer | Recovery (%) | Osmolality (mOsm/kg) | Turbidity (NTU) |
|---|---|---|---|
| Acetate | 96 | 29 | 3 |
| Citrate | 89 | 38 | 30 |
| Histidine | 93 | 61 | 6 |

2.2. Osmolality

The osmolality values of the DP formulations relevant to the DoE1 screening were comprised in the range 299-396 mOsm/kg, with most formulations having osmolalities below around 360 mOsm/kg.

The measurements were carried out at time 0, upon manufacturing completion.

The values obtained were in line with target (acceptable range 250-400 mOsm/Kg). Solutions containing Trehalose dihydrate showing higher values (close to 400 mOsm/kg) due to effect of this ingredient on freezing point and subsequent (apparent) increase in osmolality.

2.3 Thermal Stress 2.3.1 Protein Content

As determined by OD measurements, the time 0 content values were in line with theoretical values (10 mg/mL). No significant changes were observed after 1 month at 40° C.

2.3.2 Total Aggregates

Total aggregates DoE1 formulations were determined yb SE-HPLC at time 0 and after 2 and 4 weeks of storage at 40° C.

No statistically significant variations in terms of aggregates upon thermal stress at 40° C. could be highlighted, thus indicating that the different matrices tested led to invariant/ negligible changes in the aggregation pattern.

2.3.3 Fragmentation

Fragmentation by Bioanalyzer (2100 Bioanalyzer, Agilent) in DoE1 formulations was determined at time 0 and after 2 and 4 weeks of storage at 40° C.

The data indicated that:
- pH is a critical factor to protein fragmentation at 40° C. At pH>5.75, fragmentation tends to significantly increase (most typically in formulations from DoE1-13 to DoE1-19, in citrate and histidine buffers).
- The formulations presenting the lowest variations in fragmentation are those in a pH range of 5.0-5.75 preferably in presence of either D-Mannitol or Trehalose dihydrate (DoE1-2-8-9-10-12).
- Formulation DoE1-7 (citrate buffer at pH 5.25, in presence of D-Mannitol and Tween 20) presented abnormal profiles with consistent peak doubling (some issues might be related to usage of citrate as a buffering agent in terms of fragmentation, in addition to those already highlighted during manufacturing with the increase in turbidity/opalescence).

2.3.4 Turbidity

Turbidity by nephelometry in DoE1 formulations was determined at time 0 and after 2 and 4 weeks of storage at 40° C.

Opalescence/strong opalescence consistently observed in all DP formulations containing citrate as a pH buffering agent.

All formulations in sodium acetate and histidine were found to be clear/slightly opalescent with no significant changes observed over 1 month of storage at 40° C.

2.3.5 pH

No pH changes were observed.

2.4 Mechanical Stress

The DoE1 formulations were subjected to 24-hour orbital shaking in vials at 300 rpm (room temperature). Upon stress termination the samples were tested for aggregates and opalescence.

2.4.1 Total Aggregates

Total aggregates were determined by SE-HPLC after mechanical stress and compared to time 0 results. Negligible changes were observed.

2.4.2 Turbidity

Turbidity of DoE1 formulations was determined by nephelometry (2100AN IS, Hach Lange) after mechanical stress and compared to time 0 results. The data were evaluated by ANOVA and a moderately significant impact deriving from surfactant presence (0.01<p-value<0.05) was observed. Either Tween 20 or Poloxamer 188 can help minimize turbidity changes after mechanical stress.

2.5 Light Exposure

The DoE1 formulations were subjected to 7-hour irradiation at 765 W/m$^2$ (Suntest CPS, Atlas). Upon light stress termination the samples were tested for aggregates, opalescence, pH and isoforms profile.

2.5.1 Total Aggregates

Using SE-HPLC (Alliance, Waters) slight variations were observed, most frequently when sodium citrate buffer is used (p-value<0.01).

Sodium acetate and histidine are the buffers to be preferred in order to minimize aggregation changes.

2.5.2 Turbidity

As determined by nephelometry the most evident turbidity increases were typically found in citrate buffer at pH values>5.75 (DoE1-13 and DoE1-16 and DoE1-17).

2.5.3 pH

No changes were observed.

2.6 DoE1: Outcome

The data obtained in the frame of the thermal, mechanical and light stress were evaluated in order to determine conditions that provide maximal protein resistance against stresses.

The results of the analysis are reported in Table 4.

TABLE 4

Components of highly stabilized Avelumab formulations at 10 mg/mL protein concentration

| ID # | Buffer | pH | Excipient | Surfactant |
|---|---|---|---|---|
| Extrapolated | 10 mM Acetate | 5.20 | Trehalose dihydrate (280 mM) | Tween 20 (0.5 mg/mL) |
| DoE1-4 | 10 mM Acetate | 5.25 | Trehalose dihydrate (280 mM) | Tween 20 (0.2 mg/mL) |

The extrapolated formulation is highlighted in green (ID #=Extrapolated), whilst the most similar formula in the set of those tested is the DoE1-4, also reported. These data demonstrate that acetate buffer pH 5.0-5.5 provides improved protein stability, and that surfactant presence, such as either Tween 20 or Poloxamer 188, at concentrations higher than 0.2 mg/mL, is also important for improved protein stability in the formulation.

Example 3

A second DoE screening "DoE2" aimed at fine-tuning the formulations selected upon DoE1 completion and concurrently increasing protein concentration to 20 mg/mL.

With this second formulation screening, six formulations at 20 mg/mL protein concentration varying in excipients (D-Mannitol, Trehalose dihydrate) and surfactant (no surfactant, Poloxamer 188 or Polysorbate 20 at 0.5 mg/mL) in presence of 10 mM sodium acetate buffer pH 5.2 were tested after thermal stress (1 month at 40° C., 8 weeks at 25° C. and 2-8° C.) and mechanical shaking (24 hours at 300 rpm, room temperature). The relevant compositions are listed in Table 5.

TABLE 5

DoE2 screening formulations (protein concentration = 20 mg/mL)

| ID | Avelumab (mg/mL) | Buffer | Excipient | Surfactant |
|---|---|---|---|---|
| DoE2-1 | 20 | 10 mM acetate pH 5.2 | Mannitol (51 mg/mL[1]) | — |
| DoE2-2 | 20 | 10 mM acetate pH 5.2 | Trehalose dihydrate (106 mg/mL[1]) | — |
| DoE2-3 | 20 | 10 mM acetate pH 5.2 | Mannitol (51 mg/mL[1]) | Tween 20 (0.5 mg/mL) |
| DoE2-4 | 20 | 10 mM acetate pH 5.2 | Trehalose dihydrate (106 mg/mL[1]) | Tween 20 (0.5 mg/mL) |
| DoE2-5 | 20 | 10 mM acetate pH 5.2 | Mannitol (51 mg/mL[1]) | Poloxamer 188 (0.5 mg/mL) |
| DoE2-6 | 20 | 10 mM acetate pH 5.2 | Trehalose dihydrate (106 mg/mL[1]) | Poloxamer 188 (0.5 mg/mL) |
| DoE1-8 | 20 | 10 mM acetate pH 5.5 | Mannitol (51 mg/mL[1]) | Tween 20 (0.5 mg/mL) |
| Reference | 20 | 10 mM acetate pH 5.5 | Mannitol (51 mg/mL)/L-Methionine (0.21 mg/mL) | Tween 20 (0.5 mg/mL) |

The DoE2 study was conducted to comparatively evaluate the effect of D-Mannitol vs. Trehalose dihydrate, and the impact of surfactant (either Tween 20 or Poloxamer 188, or no surfactant) in sodium acetate buffer at pH 5.2, at the increased protein concentration of 20 mg/mL. Two pH 5.5 reference samples have been included in the design: "Reference" with L-Methionine, and a reference formulation without L-Methionine, corresponding to DoE1-8.

3.1 Manufacturing

The pre-formulated drug substance (DS) (27.1 mg/mL Avelumab in 10 mM sodium acetate pH 5.5) was used. The required excipients were then added to the DS material.

The sequence of addition of ingredients to the DS solution was as follows: Add D-Mannitol or Trehalose dihydrate, stir until complete dissolution, add Poloxamer 188 or Polysorbate 20 (20 mg/mL stock solution), stir until complete dissolution, add L-Methionine and stir until complete dissolution (only for Reference), stir until complete dissolution, check pH and adjust to target with sodium hydroxide or diluted acetic acid. The solutions were weight adjusted to the target with relevant buffer so as to obtain the DP compositions listed in Table 6.

DP solutions were filled (8 mL) in DINER vials.

3.2 Thermal Stress 3.2.1 Protein Content

No protein content (OD, Lambda 35, Perkin Elmer) changes observed over 4 weeks at 40° C. (Table 6) and 8 weeks at 25° C. (Table 7).

TABLE 6

Protein content (mg/mL) by OD of DoE2 formulations (thermal stress at 40° C.)

| # | ID | Protein conc (mg/mL) | Buffer | Excipient (280 mM) | Surfactant | Time 0 | 2 weeks (40° C.) | 4 weeks (40° C.) |
|---|---|---|---|---|---|---|---|---|
| 1 | DoE2-1 | 20 | 10 mM acetate pH 5.2 | D-Mannitol | No | 22.3 | 20.0 | 20.9 |
| 2 | DoE2-2 | 20 | 10 mM acetate pH 5.2 | Trehalose dihydrate | No | 22.0 | 20.6 | 21.6 |
| 3 | DoE2-3 | 20 | 10 mM acetate pH 5.2 | D-Mannitol | Tween 20 (0.5 mg/mL) | 21.9 | 20.5 | 21.6 |
| 4 | DoE2-4 | 20 | 10 mM acetate pH 5.2 | Trehalose dihydrate | Tween 20 | 22.1 | 20.5 | 22.3 |
| 5 | DoE2-5 | 20 | 10 mM acetate pH 5.2 | D-Mannitol | Lutrol F-68 (0.5 mg/mL) | 21.7 | 20.7 | 22.8 |
| 6 | DoE2-6 | 20 | 10 mM acetate pH 5.2 | Trehalose dihydrate | Lutrol F-68 (0.5 mg/mL) | 22.7 | 21.3 | 22.5 |
| 7 | DoE1-8 | 20 | 10 mM acetate pH 5.5 | D-Mannitol | Tween 20 (0.5 mg/mL) | 21.5 | 20.5 | 23.5 |

TABLE 6-continued

Protein content (mg/mL) by OD of DoE2 formulations (thermal stress at 40° C.)

| # | ID | Protein conc (mg/mL) | Buffer | Excipient (280 mM) | Surfactant | Time 0 | 2 weeks (40° C.) | 4 weeks (40° C.) |
|---|---|---|---|---|---|---|---|---|
| 8 | Reference | 20 | 10 mM acetate pH 5.5 | D-Mannitol + L-Methionine | Tween 20 (0.5 mg/mL) | 21.5 | 20.4 | 23.3 |

TABLE 7

Protein content (mg/mL) by OD of DoE2 formulations (thermal stress at 25° C.)

| # | ID | Protein conc (mg/mL) | Buffer | Excipient (280 mM) | Surfactant | Time 0 | 8 weeks (25° C.) |
|---|---|---|---|---|---|---|---|
| 1 | DoE2-1 | 20 | 10 mM acetate pH 5.2 | D-Mannitol | No | 22.3 | 20.6 |
| 2 | DoE2-2 | 20 | 10 mM acetate pH 5.2 | Trehalose dihydrate | No | 22.0 | 21.0 |
| 3 | DoE2-3 | 20 | 10 mM acetate pH 5.2 | D-Mannitol | Tween 20 (0.5 mg/mL) | 21.9 | 21.3 |
| 4 | DoE2-4 | 20 | 10 mM acetate pH 5.2 | Trehalose dihydrate | Tween 20 (0.5 mg/mL) | 22.1 | 21.5 |
| 5 | DoE2-5 | 20 | 10 mM acetate pH 5.2 | D-Mannitol | Lutrol F-68 (0.5 mg/mL) | 21.7 | 20.5 |
| 6 | DoE2-6 | 20 | 10 mM acetate pH 5.2 | Trehalose dihydrate | Lutrol F-68 (0.5 mg/mL) | 22.7 | 21.0 |
| 7 | DoE1-8 | 20 | 10 mM acetate pH 5.5 | D-Mannitol | Tween 20 (0.5 mg/mL) | 21.5 | 21.1 |
| 8 | Reference | 20 | 10 mM acetate pH 5.5 | D-Mannitol + L-Methionine | Tween 20 (0.5 mg/mL) | 21.5 | 21.2 |

3.2.2 Total Aggregates

Figure 6:
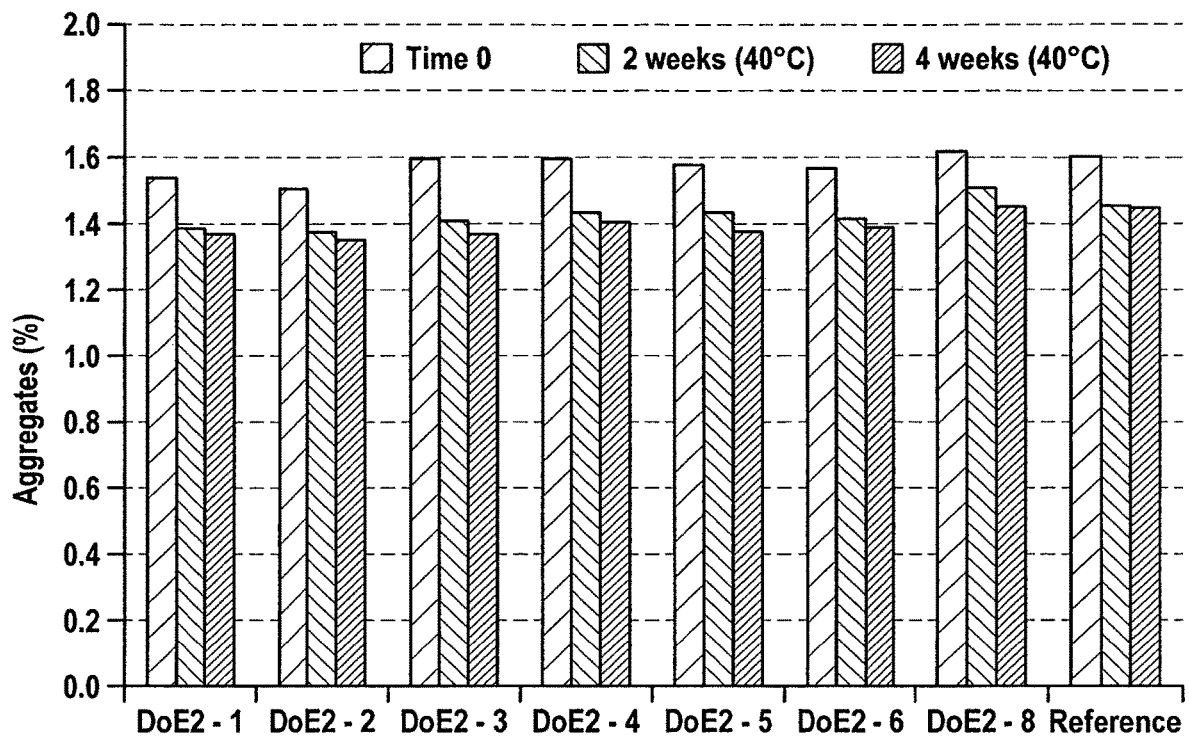
Figure 7:
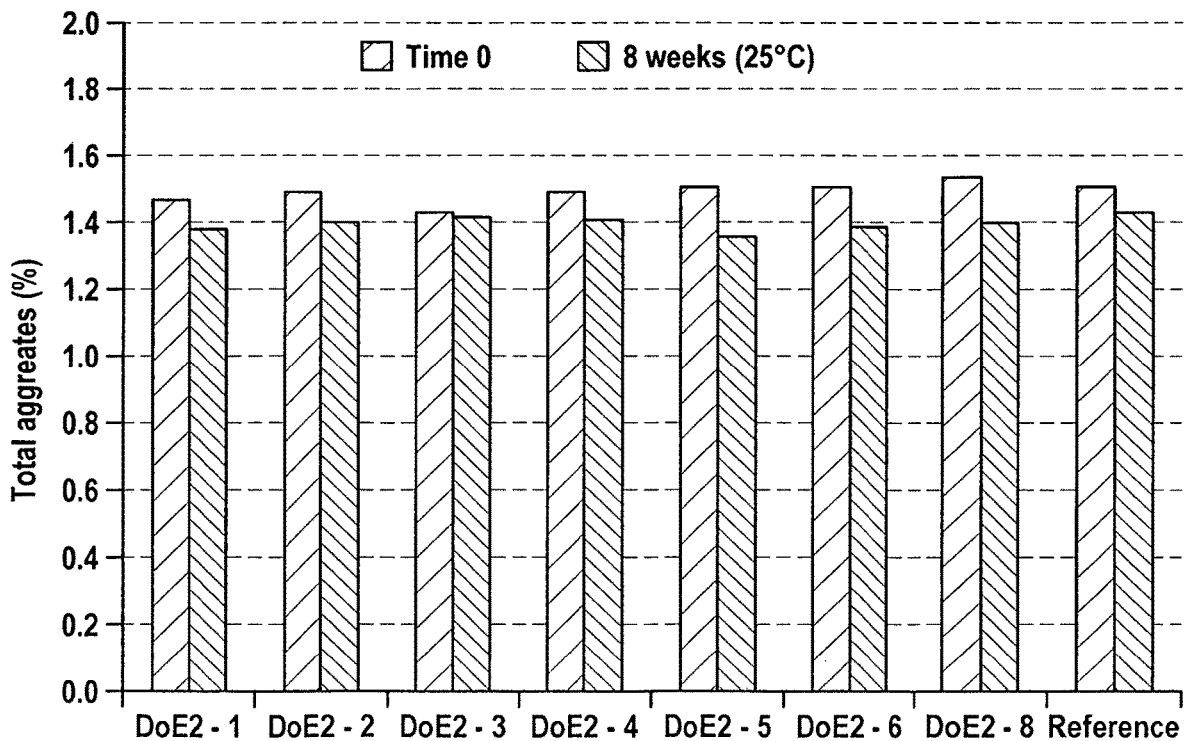

Total aggregates determined by SE-HPLC over stability at 40° C. and 25° C. are represented in FIGS. 6 and 7 respectively. Only minor, non-significant changes in aggregation were observed.

3.2.3 Fragmentation by Bioanalyzer

Fragments were evaluated over 1 month at 40° C. and after 2 months at 25° C. The relevant results are shown in FIG. 8 and FIG. 9 respectively.

At 40° C., aside from formulation DoE2-1, which presented an amount of fragments higher than 7% after 1 month, the other formulas were observed to have similar behavior (4-6% in fragments after 1 month) with slightly better performances of formulations DoE2-4, DoE2-5 and DoE2-6 (4.0-4.5% in fragments after 1 month at 40° C.)

At 25° C., similar fragmentation percentages were found after 2 months (4.6-6.1%)

3.2.4 Isoforms Profile

The isoforms profile by iCE280 (Fast IEF Analyzer, Convergent Bioscience) in DoE2 formulations was determined at time 0 and after 4 weeks of storage at 40° C. Upon storage at 40° C. typically increases in the acidic cluster can be determined, while a concurrent decrease in the basic isoforms is observed.

The isoforms profiles were evaluated over 1 month at 40° C. (Table 8) and after 8 weeks at 25° C. (FIG. 10).

Comparable variations were observed in all samples at both stressing conditions.

TABLE 8 iCE280 results for DoE2 formulations after 4 weeks at 40° C.

| | Time 0 | | | 4 weeks at 40° C. | | |
|---|---|---|---|---|---|---|
| | Acidic forms (%) | Main peak (%) | Basic forms (%) | Acidic forms (%) | Main peak (%) | Basic forms (%) |
| DoE2-1 | 32.3 | 36.0 | 31.7 | 40.3 | 31.9 | 27.8 |
| DoE2-2 | 32.0 | 37.7 | 30.4 | 38.0 | 33.6 | 28.5 |
| DoE2-3 | 32.2 | 36.7 | 31.1 | 39.9 | 32.7 | 27.5 |
| DoE2-4 | 32.7 | 36.7 | 30.6 | 39.7 | 33.0 | 27.3 |
| DoE2-5 | 32.5 | 37.4 | 30.2 | 38.1 | 33.4 | 28.5 |
| DoE2-6 | 32.4 | 37.0 | 30.7 | 38.3 | 33.7 | 28.0 |
| DoE1-8 | 33.2 | 36.9 | 30.0 | 38.8 | 33.5 | 27.7 |
| Reference | 32.2 | 36.2 | 31.7 | 37.7 | 33.4 | 28.9 |

3.2.6 Turbidity

No variations observed after 1 month at 40° C. (Table 9) and 2 months at 25° C. (Table 10).

TABLE 9

Turbidity of DoE2 formulations after 1 month at 40° C.

| # | ID | Protein conc (mg/mL) | Buffer | Excipient (280 mM) | Surfactant | Time 0 | 2 weeks (40° C.) | 4 weeks (40° C.) |
|---|---|---|---|---|---|---|---|---|
| 1 | DoE2-1 | 20 | 10 mM acetate pH 5.2 | D-Mannitol | No | 2 | 2 | 2 |
| 2 | DoE2-2 | 20 | 10 mM acetate pH 5.2 | Trehalose dihydrate | No | 2 | 2 | 2 |
| 3 | DoE2-3 | 20 | 10 mM acetate pH 5.2 | D-Mannitol | Tween 20 (0.5 mg/mL) | 2 | 2 | 2 |
| 4 | DoE2-4 | 20 | 10 mM acetate pH 5.2 | Trehalose dihydrate | Tween 20 (0.5 mg/mL) | 2 | 2 | 2 |
| 5 | DoE2-5 | 20 | 10 mM acetate pH 5.2 | D-Mannitol | Lutrol F-68 (0.5 mg/mL) | 2 | 2 | 2 |
| 6 | DoE2-6 | 20 | 10 mM acetate pH 5.2 | Trehalose dihydrate | Lutrol F-68 (0.5 mg/mL) | 2 | 2 | 2 |
| 7 | DoE1-8 | 20 | 10 mM acetate pH 5.5 | D-Mannitol | Tween 20 (0.5 mg/mL) | 2 | 2 | 2 |
| 8 | Reference | 20 | 10 mM acetate pH 5.5 | D-Mannitol + L-Methionine | Tween 20 (0.5 mg/mL) | 3 | 3 | 2 |

TABLE 10

Turbidity of DoE2 formulations after 2 months at 25° C.

| # | ID | Protein conc (mg/mL) | Buffer | Excipient (280 mM) | Surfactant | Time 0 | 8 weeks (25° C.) |
|---|---|---|---|---|---|---|---|
| 1 | DoE2-1 | 20 | 10 mM acetate pH 5.2 | D-Mannitol | No | 2 | 2 |
| 2 | DoE2-2 | 20 | 10 mM acetate pH 5.2 | Trehalose dihydrate | No | 2 | 2 |
| 3 | DoE2-3 | 20 | 10 mM acetate pH 5.2 | D-Mannitol | Tween 20 (0.5 mg/mL) | 2 | 2 |
| 4 | DoE2-4 | 20 | 10 mM acetate pH 5.2 | Trehalose dihydrate | Tween 20 (0.5 mg/mL) | 2 | 2 |
| 5 | DoE2-5 | 20 | 10 mM acetate pH 5.2 | D-Mannitol | Lutrol F-68 (0.5 mg/mL) | 2 | 2 |
| 6 | DoE2-6 | 20 | 10 mM acetate pH 5.2 | Trehalose dihydrate | Lutrol F-68 (0.5 mg/mL) | 2 | 2 |
| 7 | DoE1-8 | 20 | 10 mM acetate pH 5.5 | D-Mannitol | Tween 20 (0.5 mg/mL) | 2 | 3 |
| 8 | Reference | 20 | 10 mM acetate pH 5.5 | D-Mannitol + L-Methionine | Tween 20 (0.5 mg/mL) | 3 | 3 |

3.2.7 pH

No variations observed after 1 month at 40° C. (Table 11) and 2 months at 25° C. (Table 12).

TABLE 11 pH of DoE2 formulations after 1 month at 40° C.

| # | ID | Protein conc (mg/mL) | Buffer | Excipient (280 mM) | Surfactant | Time 0 | 2 weeks (40° C.) | 4 weeks (40° C.) |
|---|---|---|---|---|---|---|---|---|
| 1 | DoE2-1 | 20 | 10 mM acetate pH 5.2 | D-Mannitol | No | 5.2 | 5.2 | 5.2 |
| 2 | DoE2-2 | 20 | 10 mM acetate pH 5.2 | Trehalose dihydrate | No | 5.2 | 5.2 | 5.2 |

TABLE 11-continued pH of DoE2 formulations after 1 month at 40° C.

| # | ID | Protein conc (mg/mL) | Buffer | Excipient (280 mM) | Surfactant | Time 0 | 2 weeks (40° C.) | 4 weeks (40° C.) |
|---|---|---|---|---|---|---|---|---|
| 3 | DoE2-3 | 20 | 10 mM acetate pH 5.2 | D-Mannitol | Tween 20 (0.5 mg/mL) | 5.2 | 5.2 | 5.2 |
| 4 | DoE2-4 | 20 | 10 mM acetate pH 5.2 | Trehalose dihydrate | Tween 20 (0.5 mg/mL) | 5.2 | 5.2 | 5.2 |
| 5 | DoE2-5 | 20 | 10 mM acetate pH 5.2 | D-Mannitol | Lutrol F-68 (0.5 mg/mL) | 5.2 | 5.2 | 5.2 |
| 6 | DoE2-6 | 20 | 10 mM acetate pH 5.2 | Trehalose dihydrate | Lutrol F-68 (0.5 mg/mL) | 5.2 | 5.2 | 5.2 |
| 7 | DoE1-8 | 20 | 10 mM acetate pH 5.5 | D-Mannitol | Tween 20 (0.5 mg/mL) | 5.5 | 5.5 | 5.5 |
| 8 | Reference | 20 | 10 mM acetate pH 5.5 | D-Mannitol + L-Methionine | Tween 20 (0.5 mg/mL) | 5.5 | 5.5 | 5.5 |

TABLE 12 pH of DoE2 formulations after 2 months at 25° C.

| # | ID | Protein conc (mg/mL) | Buffer | Excipient (280 mM) | Surfactant | Time 0 | 8 weeks (25° C.) |
|---|---|---|---|---|---|---|---|
| 1 | DoE2-1 | 20 | 10 mM acetate pH 5.2 | D-Mannitol | No | 5.2 | 5.2 |
| 2 | DoE2-2 | 20 | 10 mM acetate pH 5.2 | Trehalose dihydrate | No | 5.2 | 5.2 |
| 3 | DoE2-3 | 20 | 10 mM acetate pH 5.2 | D-Mannitol | Tween 20 (0.5 mg/mL) | 5.2 | 5.3 |
| 4 | DoE2-4 | 20 | 10 mM acetate pH 5.2 | Trehalose dihydrate | Tween 20 (0.5 mg/mL) | 5.2 | 5.2 |
| 5 | DoE2-5 | 20 | 10 mM acetate pH 5.2 | D-Mannitol | Lutrol F-68 (0.5 mg/mL) | 5.2 | 5.2 |
| 6 | DoE2-6 | 20 | 10 mM acetate pH 5.2 | Trehalose dihydrate | Lutrol F-68 (0.5 mg/mL) | 5.2 | 5.2 |
| 7 | DoE1-8 | 20 | 10 mM acetate pH 5.5 | D-Mannitol | Tween 20 (0.5 mg/mL) | 5.5 | 5.5 |
| 8 | Reference | 20 | 10 mM acetate pH 5.5 | D-Mannitol + L-Methionine | Tween 20 (0.5 mg/mL) | 5.5 | 5.6 |

3.2.8 Circular Dichroism

CD spectra (J-810 Spectropolarimeter, Jasco) of DoE2 formulations were collected at time 0 and after 4 weeks at 40° C. and 8 weeks at 25° C. in the near UV range. Protein in all formulation generally retains its tertiary structure after 4 weeks at 40° C. and 8 weeks at 25° C.

3.2.9 Sub-Visible Particles

The sub-visible particles of the DoE2 formulations after 8 weeks of storage at 2-8° C. were determined. The results are shown in Table 13. The values were found within European Pharmacopoeia limits (for solutions supplied in containers with a nominal content of less than 100 mL).

TABLE 13

Sub-visible particles of DoE2 formulations after 8 weeks at 2-8° C.

| # | ID | Protein conc (mg/mL) | Buffer | Excipient (280 mM) | Surfactant | Sub-visible particles >10 μm (per container) | Sub-visible particles >25 μm (per container) |
|---|---|---|---|---|---|---|---|
| 1 | DoE2-1 | 20 | 10 mM acetate pH 5.2 | D-Mannitol | No | 754 | 33 |
| 2 | DoE2-2 | 20 | 10 mM acetate pH 5.2 | Trehalose dihydrate | No | 716 | 14 |

TABLE 13-continued

Sub-visible particles of DoE2 formulations after 8 weeks at 2-8° C.

| # | ID | Protein conc (mg/mL) | Buffer | Excipient (280 mM) | Surfactant | Sub-visible particles >10 μm (per container) | Sub-visible particles >25 μm (per container) |
|---|---|---|---|---|---|---|---|
| 3 | DoE2-3 | 20 | 10 mM acetate pH 5.2 | D-Mannitol | Tween 20 (0.5 mg/mL) | 597 | 24 |
| 4 | DoE2-4 | 20 | 10 mM acetate pH 5.2 | Trehalose dihydrate | Tween 20 (0.5 mg/mL) | 1839 | 100 |
| 5 | DoE2-5 | 20 | 10 mM acetate pH 5.2 | D-Mannitol | Lutrol F-68 (0.5 mg/mL) | 431 | 38 |
| 6 | DoE2-6 | 20 | 10 mM acetate pH 5.2 | Trehalose dihydrate | Lutrol F-68 (0.5 mg/mL) | 521 | 28 |
| 7 | DoE1-8 | 20 | 10 mM acetate pH 5.5 | D-Mannitol | Tween 20 (0.5 mg/mL) | 915 | 14 |
| 8 | Reference | 20 | 10 mM acetate pH 5.5 | D-Mannitol + L-Methionine | Tween 20 (0.5 mg/mL) | 1873 | 52 |

3.3 Mechanical Stress 3.3.1 Fragmentation by Bioanalyzer

After 24 hours at 300 rpm, slight variations in fragments (Table 14) were observed in all samples (up to 5.0-6.5%) with no specific relation to the specific compositions tested.

TABLE 14

Fragments (%) by Bioanalyzer of DoE2 formulations after 24-hour shaking (300 rpm; room temperature)

| # | ID | Protein conc (mg/mL) | Buffer | Excipient (280 mM) | Surfactant | Time 0 | 24 H 300 RPM |
|---|---|---|---|---|---|---|---|
| 1 | DoE2-1 | 20 | 10 mM acetate pH 5.2 | D-Mannitol | No | 4.9 | 5.5 |
| 2 | DoE2-2 | 20 | 10 mM acetate pH 5.2 | Trehalose dihydrate | No | 4.6 | 5.0 |
| 3 | DoE2-3 | 20 | 10 mM acetate pH 5.2 | D-Mannitol | Tween 20 (0.5 mg/mL) | 4.7 | 5.7 |
| 4 | DoE2-4 | 20 | 10 mM acetate pH 5.2 | Trehalose dihydrate | Tween 20 (0.5 mg/mL) | 4.6 | 6.5 |
| 5 | DoE2-5 | 20 | 10 mM acetate pH 5.2 | D-Mannitol | Lutrol F-68 (0.5 mg/mL) | 5.1 | 6.2 |
| 6 | DoE2-6 | 20 | 10 mM acetate pH 5.2 | Trehalose dihydrate | Lutrol F-68 (0.5 mg/mL) | 5.2 | 5.3 |
| 7 | DoE1-8 | 20 | 10 mM acetate pH 5.5 | D-Mannitol | Tween 20 (0.5 mg/mL) | 3.5 | 5.4 |
| 8 | Reference | 20 | 10 mM acetate pH 5.5 | D-Mannitol + L-Methionine | Tween 20 (0.5 mg/mL) | 3.4 | 5.4 |

3.3.2 Aggregates

No changes were observed after mechanical shaking (Table 15).

TABLE 15

Aggregates (%) by SE-HPLC of DoE2 formulations after 24-hour shaking (300 rpm; room temperature)

| # | ID | Protein conc (mg/mL) | Buffer | Excipient (280 mM) | Surfactant | Time 0 | 24 H 300 RPM |
|---|---|---|---|---|---|---|---|
| 1 | DoE2-1 | 20 | 10 mM acetate pH 5.2 | D-Mannitol | No | 1.5 | 1.5 |

TABLE 15-continued

Aggregates (%) by SE-HPLC of DoE2 formulations after 24-hour shaking (300 rpm; room temperature)

| # | ID | Protein conc (mg/mL) | Buffer | Excipient (280 mM) | Surfactant | Time 0 | 24 H 300 RPM |
|---|---|---|---|---|---|---|---|
| 2 | DoE2-2 | 20 | 10 mM acetate pH 5.2 | Trehalose dihydrate | No | 1.5 | 1.5 |
| 3 | DoE2-3 | 20 | 10 mM acetate pH 5.2 | D-Mannitol | Tween 20 (0.5 mg/mL) | 1.6 | 1.5 |
| 4 | DoE2-4 | 20 | 10 mM acetate pH 5.2 | Trehalose dihydrate | Tween 20 (0.5 mg/mL) | 1.6 | 1.5 |
| 5 | DoE2-5 | 20 | 10 mM acetate pH 5.2 | D-Mannitol | Lutrol F-68 (0.5 mg/mL) | 1.6 | 1.5 |
| 6 | DoE2-6 | 20 | 10 mM acetate pH 5.2 | Trehalose dihydrate | Lutrol F-68 (0.5 mg/mL) | 1.6 | 1.6 |
| 7 | DoE1-8 | 20 | 10 mM acetate pH 5.5 | D-Mannitol | Tween 20 (0.5 mg/mL) | 1.6 | 1.6 |
| 8 | Reference | 20 | 10 mM acetate pH 5.5 | D-Mannitol + L-Methionine | Tween 20 (0.5 mg/mL) | 1.6 | 1.6 |

3.3.3 pH

No changes were observed after mechanical shaking (Table 16).

TABLE 16 pH of DoE2 formulations after 24-hour shaking (300 rpm; room temperature)

| # | ID | Protein conc (mg/mL) | Buffer | Excipient (280 mM) | Surfactant | Time 0 | 24 H 300 rpm |
|---|---|---|---|---|---|---|---|
| 1 | DoE2-1 | 20 | 10 mM acetate pH 5.2 | D-Mannitol | No | 5.2 | 5.2 |
| 2 | DoE2-2 | 20 | 10 mM acetate pH 5.2 | Trehalose dihydrate | No | 5.2 | 5.2 |
| 3 | DoE2-3 | 20 | 10 mM acetate pH 5.2 | D-Mannitol | Tween 20 (0.5 mg/mL) | 5.2 | 5.2 |
| 4 | DoE2-4 | 20 | 10 mM acetate pH 5.2 | Trehalose dihydrate | Tween 20 (0.5 mg/mL) | 5.2 | 5.2 |
| 5 | DoE2-5 | 20 | 10 mM acetate pH 5.2 | D-Mannitol | Lutrol F-68 (0.5 mg/mL) | 5.2 | 5.2 |
| 6 | DoE2-6 | 20 | 10 mM acetate pH 5.2 | Trehalose dihydrate | Lutrol F-68 (0.5 mg/mL) | 5.2 | 5.2 |
| 7 | DoE1-8 | 20 | 10 mM acetate pH 5.5 | D-Mannitol | Tween 20 (0.5 mg/mL) | 5.5 | 5.5 |
| 8 | Reference | 20 | 10 mM acetate pH 5.5 | D-Mannitol + L-Methionine | Tween 20 (0.5 mg/mL) | 5.5 | 5.5 |

3.4 Turbidity

No changes were observed after mechanical shaking (Table 17).

TABLE 17

Turbidity (NTU) of DoE2 formulations after 24-hour shaking (300 rpm; room temperature)

| # | ID | Protein conc (mg/mL) | Buffer | Excipient (280 mM) | Surfactant | Time 0 | 24 h 300 rpm |
|---|---|---|---|---|---|---|---|
| 1 | DoE2-1 | 20 | 10 mM acetate pH 5.2 | D-Mannitol | No | 2 | 2 |
| 2 | DoE2-2 | 20 | 10 mM acetate pH 5.2 | Trehalose dihydrate | No | 2 | 2 |
| 3 | DoE2-3 | 20 | 10 mM acetate pH 5.2 | D-Mannitol | Tween 20 (0.5 mg/mL) | 2 | 2 |
| 4 | DoE2-4 | 20 | 10 mM acetate pH 5.2 | Trehalose dihydrate | Tween 20 (0.5 mg/mL) | 2 | 2 |
| 5 | DoE2-5 | 20 | 10 mM acetate pH 5.2 | D-Mannitol | Lutrol F-68 (0.5 mg/mL) | 2 | 2 |

TABLE 17-continued

Turbidity (NTU) of DoE2 formulations after
24-hour shaking (300 rpm; room temperature)

| # | ID | Protein conc (mg/mL) | Buffer | Excipient (280 mM) | Surfactant | Time 0 | 24 h 300 rpm |
|---|---|---|---|---|---|---|---|
| 6 | DoE2-6 | 20 | 10 mM acetate pH 5.2 | Trehalose dihydrate | Lutrol F-68 (0.5 mg/mL) | 2 | 2 |
| 7 | DoE1-8 | 20 | 10 mM acetate pH 5.5 | D-Mannitol | Tween 20 (0.5 mg/mL) | 2 | 2 |
| 8 | Reference | 20 | 10 mM acetate pH 5.5 | D-Mannitol + L-Methionine | Tween 20 (0.5 mg/mL) | 3 | 2 |

3.5 DoE2: Outcome

These results demonstrate that pH 5.2 (extrapolated from DoE1) does not impact fragmentation and therefore is suitable for use in a stable formulation. Optimal pH for preserving protein stability was demonstrated to be in the range 5.0-5.5 (DoE1). In contrast, pH values of 5.6-5.7 could result in higher fragmentation.

Mannitol and Trehalose dihydrate resulted in similar behavior.

No superiority of Poloxamer 188 over Tween 20 was found.

These results also demonstrate that higher protein concentration (20 mg/mL) in the DoE2 formulation is feasible with no observed or anticipated stability issues.

DoE2: Formulation 3 (the formula most preferred and finally selected for further use at 20 mg/mL) was compared in terms of isoforms profiles to the reference formula at time 0, after 4 weeks at 40° C. and 8 weeks at 25° C. in order to evaluate whether different behavior between the two formulas are present over stability time at different conditions. The results are presented in Table 18.

TABLE 18

Isoforms profiles by iCE280 of DoE2 Formulation 3 and Reference
formulation at time 0, after 4 weeks (40° C.) and 8 weeks (25° C.)

| ID# | Buffer | pH | Excipient | Surfactant | Cluster | Time 0 | 4 weeks (40° C.) | 8 weeks (25° C.) |
|---|---|---|---|---|---|---|---|---|
| DoE2-3 | 10 mM Acetate | 5.20 | D-Mannitol | Tween 20 (0.5 mg/mL) | 1 | 1.6 | 3.1 | 2.9 |
| | | | | | 2 | 4.5 | 5.3 | 7.1 |
| | | | | | 3 | 9.9 | 10.8 | 9.1 |
| | | | | | 4 | 16.2 | 20.7 | 18.0 |
| | | | | | 5 | 36.7 | 32.7 | 34.9 |
| | | | | | 6 | 22.2 | 19.7 | 20.3 |
| | | | | | 7 | 8.9 | 7.8 | 7.7 |
| Reference | 10 mM Acetate | 5.50 | Mannitol + L-Methionine | Tween 20 (0.5 mg/mL) | 1 | 1.8 | 2.3 | 3.4 |
| | | | | | 2 | 4.3 | 5.0 | 8.1 |
| | | | | | 3 | 9.8 | 10.6 | 10.0 |
| | | | | | 4 | 16.3 | 19.8 | 16.9 |
| | | | | | 5 | 36.2 | 33.4 | 34.7 |
| | | | | | 6 | 22.6 | 21.1 | 19.6 |
| | | | | | 7 | 9.1 | 7.8 | 7.4 |

Also the additional timepoint (8 weeks) at 25° C. highlighted no major issues deriving from the reduced pH with respect to the reference formulation.

Example 4—Effect of Antioxidant (L-Methionine)

As methionine was used in the formulation disclosed in WO2013079174, the present Avelumab formulation development aimed to also clarify the impact of this compound as an antioxidant.

The 10 mg/mL samples (from the DoE1 set) were 2-fold diluted with 200 μL of 6% $H_2O_2$, obtaining a final protein concentration of about 5 mg/mL and 3% $H_2O_2$, and then incubated 3 h at 5° C. At the end of the incubation the sample was washed versus water by ultracentrifugation using an Amicon Ultra (Millipore) 4 mL 10 kDa (4 washes 1 mL each step). The final protein concentration after Amicon treatment was about 10 mg/mL.

DoE1: Formulation 8 is identical to Reference formula of DoE2, except for the presence of L-Methionine: the forced oxidation with $H_2O_2$ (3 hours at 2-8° C.) of the two formulas and following testing by iCE280 (oxidation generally leads to increase in more acidic species in electropherograms) and Bioanalyzer aimed to determine whether any differences arise in the two formulations due to the presence of the antioxidant agent. The results are presented in Tables 19 and 20.

TABLE 19

Isoforms profiles by iCE280 of DoE1 Formulation 8 and Reference formulation after forced oxidation treatment. Upper table: samples stored at 2-8° C. Bottom table: sample stored 4 weeks at 40° C. + 6 weeks at 2-8° C.

| ID# | Buffer | pH | Anti PD-L1 (mg/ml) | Excipient | Surfactant | Cluster | Oxidised with 3% $H_2O_2$ (after 10 week storage at 2-8° C.) |
|---|---|---|---|---|---|---|---|
| DoE1-8 | 10 mM Acetate | 5.50 | 10 | Mannitol (280 mM) | Tween 20 (0.5 mg/mL) | 1 | 2.2 |
| | | | | | | 2 | 4.5 |
| | | | | | | 3 | 9.8 |
| | | | | | | 4 | 23.2 |
| | | | | | | 5 | 39.0 |
| | | | | | | 6 | 16.6 |
| | | | | | | 7 | 4.8 |
| Reference | 10 mM Acetate | 5.50 | 10 | Mannitol (280 mM) + L-Methionine (1.4 mM) | Tween 20 (0.5 mg/mL) | 1 | 2.2 |
| | | | | | | 2 | 4.5 |
| | | | | | | 3 | 10.1 |
| | | | | | | 4 | 23.7 |
| | | | | | | 5 | 37.9 |
| | | | | | | 6 | 16.8 |
| | | | | | | 7 | 4.8 |

| ID# | Buffer | pH | Anti PD-L1 (mg/mL) | Excipient | Surfactant | Cluster | Oxidised with 3% $H_2O_2$ (after 4 week storage at 40° C. + 6 weeks at 2-8° C.) |
|---|---|---|---|---|---|---|---|
| DoE1-8 | 10 mM Acetate | 5.50 | 10 | Mannitol (280 mM) | Tween 20 (0.5 mg/mL) | 1 | 2.5 |
| | | | | | | 2 | 5.9 |
| | | | | | | 3 | 11.4 |
| | | | | | | 4 | 27.2 |
| | | | | | | 5 | 34.5 |
| | | | | | | 6 | 14.6 |
| | | | | | | 7 | 4.0 |
| Reference | 10 mM Acetate | 5.50 | 10 | Mannitol (280 mM) + L-Methionine (1.4 mM) | Tween 20 (0. 5 mg/mL) | 1 | 2.7 |
| | | | | | | 2 | 5.9 |
| | | | | | | 3 | 11.1 |
| | | | | | | 4 | 26.7 |
| | | | | | | 5 | 35.8 |
| | | | | | | 6 | 14.4 |
| | | | | | | 7 | 3.4 |

Comparable acidic clusters abundances were observed for the two formulations (with or w/o methionine).

Fragments by Bioanalyzer were also tested for these samples (Table 20): comparable levels of fragmentation were observed for the two formulations (with or w/o methionine).

TABLE 20

Fragments by Bioanalyzer of DoE1 Formulation 8 and Reference formulation after forced oxidation treatment. Upper table: samples stored at 2-8° C. Bottom table: sample stored 4 weeks at 40° C. + 6 weeks at 2-8° C.

| ID# | Buffer | pH | Anti PD-L1 (mg/mL) | Excipient | Surfactant | Oxidized with 3% $H_2O_2$ (after 10 week storage at 2-8° C.) |
|---|---|---|---|---|---|---|
| DoE1-8 | 10 mM Acetate | 5.50 | 10 | Mannitol (280 mM) | Tween 20 (0.5 mg/mL) | 2.4 |
| Reference | 10 mM Acetate | 5.50 | 10 | Mannitol (280 mM) + L-Methionine (1.4 mM) | Tween 20 (0.5 mg/mL) | 2.5 |

TABLE 20-continued

Fragments by Bioanalyzer of DoE1 Formulation 8 and Reference formulation after forced oxidation treatment.
Upper table: samples stored at 2-8° C.
Bottom table: sample stored 4 weeks at 40° C. + 6 weeks at 2-8° C.

| ID# | Buffer | pH | Anti PD-L1 (mg/mL) | Excipient | Surfactant | Oxidised with 3% $H_2O_2$ (after 4 week storage at 40° C. + 6 weeks at 2-8° C.) |
|---|---|---|---|---|---|---|
| DoE1-8 | 10 mM Acetate | 5.50 | 10 | Mannitol (280 mM) | Tween 20 (0.5 mg/mL) | 2.5 |
| Reference | 10 mM Acetate | 5.50 | 10 | Mannitol (280 mM) + L-Methionine (1.4 mM) | Tween 20 (0.5 mg/mL) | 3.0 |

These results suggest that an antioxidant is not needed to stabilize Avelumab and can, therefore, be omitted from the formulation.

Example 5—Long Term Stability Studies 5.1 Drug Product Compositions and Strengths The Avelumab formulations 1, 2, 3, 4 and 5 listed in Table 21 were manufactured and used for a long term stability study. The manufacturing process included a compounding followed by a sterilizing double-filtration step through a 0.22 µm membrane (PES and PVDF filters were tested) before the final filling in vials.

Formulation 5 corresponds to the Reference used also in the DoE-1 and -2 studies as described in Example 2 and 3.

TABLE 21

DP compositions

| | DP Compositions | | | | |
|---|---|---|---|---|---|
| Ingredient(s) | Formulation 1 (DP 01-190214) | Formulation 2 (DP 02-190214) | Formulation 3 (DP 03-180214) | Formulation 4 (DP 04-180214) | Reference (DP 05-190214) |
| Avelumab | 20 mg/mL | 20 mg/mL | 10 mg/mL | 10 mg/mL | 10 mg/mL |
| Sodium acetate buffer | 10 mM | 10 mM | 10 mM | 10 mM | 10 mM |
| Mannitol | 51 mg/mL | 0 mg/mL | 51 mg/mL | 0 mg/mL | 51 mg/mL |
| Trehalose Dihydrate | 0 mg/mL | 106 mg/mL | 0 mg/mL | 106 mg/mL | 0 mg/mL |
| Polysorbate 20 | 0.5 mg/mL | 0.5 mg/mL | 0.5 mg/mL | 0.5 mg/mL | 0.5 mg/mL |
| L-Methionine | 0 | 0 | 0 | 0 | 1.4 mM |
| sodium hydroxide or hydrochloric acid | q.s to pH 5.2 ± 0.1 | q.s to pH 5.2 ± 0.1 | q.s to pH 5.2 ± 0.1 | q.s to pH 5.2 ± 0.1 | q.s to pH 5.5 ± 0.1 |
| Filling volume (in Type I glass vials) | 10 mL | 10 mL | 20 mL | 20 mL | 8 mL |

Upon manufacturing (time 0), the osmolality was determined and found in line with expected value (range: 320-350 mOsm/kg).

5.2 Stability Study Plan and Duration

Concerning the stability of the formulations, the study schedule, the storage conditions and the tests to be applied are summarized in Table 22. For each time point the table indicates the storage condition to be tested.

The storage of the samples has been carried out with the vials in the upright position.

The study is to be conducted over 1 month at 40° C., 6 months at accelerated conditions (at 25° C.) and 12 months at long term conditions (2-8° C.).

TABLE 22

Stability Plan

| Test | T = 0 | 0.5M (2 wk) | 1M (4 wk) | 2M (8 wk) | 3M (13 wk) | 6M (26 wk) | 9M (39 wk) | 12M (52 wk) |
|---|---|---|---|---|---|---|---|---|
| Colour | X | 40° C. | 25° C. 40° C. | 2-8° C. 25° C. | 2-8° C. 25° C. | 2-8° C. 25° C. | 2-8° C. | 2-8° C. |
| Turbidity | X | 40° C. | 25° C. 40° C. | 2-8° C. 25° C. | 2-8° C. 25° C. | 2-8° C. 25° C. | 2-8° C. | 2-8° C. |
| pH | X | 40° C. | 25° C. 40° C. | 2-8° C. 25° C. | 2-8° C. 25° C. | 2-8° C. 25° C. | 2-8° C. | 2-8° C. |
| Content A280-A320 | X | 40° C. | 25° C. 40° C. | 2-8° C. 25° C. | 2-8° C. 25° C. | 2-8° C. 25° C. | 2-8° C. | 2-8° C. |
| SE-HPLC | X | 40° C. | 25° C. 40° C. | 2-8° C. 25° C. | 2-8° C. 25° C. | 2-8° C. 25° C. | 2-8° C. | 2-8° C. |
| SDS-page red | X | 40° C. | 25° C. 40° C. | 2-8° C. 25° C. | 2-8° C. 25° C. | 2-8° C. 25° C. | 2-8° C. | 2-8° C. |
| SDS-page non-red | X | 40° C. | 25° C. 40° C. | 2-8° C. 25° C. | 2-8° C. 25° C. | 2-8° C. 25° C. | 2-8° C. | 2-8° C. |
| iCE-280 | X | 40° C. | 25° C. 40° C. | 2-8° C. 25° C. | 2-8° C. 25° C. | 2-8° C. 25° C. | 2-8° C. | 2-8° C. |
| Osmolarity | X | 40° C. | N/A | N/A | N/A | N/A | N/A | N/A |
| Subvisible particles | X | 40° C. | 25° C. 40° C. | 2-8° C. 25° C. | 2-8° C. 25° C. | 2-8° C. 25° C. | 2-8° C. | 2-8° C. |
| Potency | X | 40° C. | 25° C. 40° C. | N/A | 2-8° C. 25° C. | 2-8° C. 25° C. | 2-8° C. | 2-8° C. |

Data were collected at 40° C. (up to 1 month), 25° C. (up to 6 months) and 2-8° C. (up to 12 months).

5.3 Stability at 2-8° C.

5.3.1 Degree of Coloration by Visual Inspection

No changes observed over stability. All solutions remain clearer than clearest standard solution (<Y7). Values within specifications.

5.3.2 Degree of Opalescence by Nephelometry

All solutions show turbidity comprised in the range of clear solutions (1-3 NTU). Values within specifications.

5.3.3 pH

No changes observed over stability. All solutions show pH values in line with target (5.2±0.1 for formulations 1 to 4 and 5.5±0.1 for Reference DP). Values within specifications.

5.3.4 Protein Content by OD

Concentration of formulations 1 and 2 (target concentration=20 mg/mL) was found in the range 18.7-19.8 mg/mL (within ±10% limits with respect to target) during the study, with no significant changes over time.

Concentration of formulations 3 and 4 and Reference DP (target concentration=10 mg/mL) was found in the range 9.3-10.2 mg/mL during the study; no significant changes found.

Protein content remains therefore unaltered over 12 month stability at 2-8° C. (Values within specifications).

5.3.5 Dimers and HMWs by SE-HPLC

No changes in aggregation over 12 months at 2-8° C. with respect to time 0. Values within specifications.

5.3.6 Fragments (LMWs) by SDS-PAGE N-Red

As shown in FIG. 11 the samples showed a time 0 value of LMWs by SDS-PAGE N-RED in the range 11.9-16.2%, followed by a +5-7% increase at the next point (8 weeks) and by minor changes over the rest of stability, up to six months.

5.3.7 Sub-Visible Particles

As for sub-visible particles per container, the counts were below the limits set by United States, European and Japanese Pharmacopoeia for solutions for infusion or injection with nominal content of less than 100 mL (6000 per container equal to or greater than 10 μm and 600 per container equal to or greater than 25 μm). The relevant bar charts for the two particle size ranges are shown in FIG. 12 and FIG. 13 respectively for sub-visible particles ≥10 μm and sub-visible particles ≥25 μm No changes in sub-visible particles upon storage were highlighted.

5.3.8 Biological Activity

Bioactivity values were typically in the range 89-110% for all time points tested in the course of the stability study. No decrease observed upon storage.

5.3.9 Isoforms Pattern

The results from iCE280 experiments are reported in FIG. 14 (acidic cluster, sum of peaks 1-2-3-4), FIG. 15 (main peak) and FIG. 16 (basic cluster, sum of peaks 6-7). Isoforms profile is retained throughout the 12 month stability period. At refrigerated conditions, no impact of pH on antibody's isoforms is observed.

5.3.10 2-8° C. Stability Outcome

None of the physico-chemical properties of the five formulations tested was found to undergo significant changes over the 12 month stability at 2-8° C. This is surprising especially for the isoforms patterns, as in formulations 1 to 4 no methionine is present.

5.4 Stability at 25° C.

5.4.1 Degree of Coloration by Visual Inspection

No changes observed over stability. All solutions remain clearer than clearest standard solution (<Y7). Values within specifications.

5.4.2 Degree of Opalescence by Nephelometry

All solutions show turbidity comprised between 1-3 NTU (clear solutions range). Values within specifications.

5.4.3 pH

No changes observed over stability. All solutions show pH values in line with target (5.2±0.1 for formulations 1-2-3-4 and 5.5±0.1 for Reference DP). Values within specifications.

5.4.4 Protein Content by OD

Concentration of formulations 1 and 2 (target concentration=20 mg/mL) was found in the range 18.5-20.0 mg/mL (within ±10% limits with respect to target) during the study, with no significant changes over time.

Concentration of formulations 3 and 4 and Reference DP (target concentration=10 mg/mL) was found in the range 9.5-10.0 mg/mL during the study; no significant changes found.

Protein content remains therefore unaltered over six-month stability at 25° C. Values within specifications.

5.4.5 Dimers and HMWs by SE-HPLC

No changes in aggregation over six months at 25° C. with respect to time 0. Aggregation lower than specification limit (not more than 5%) was found throughout the study.

5.4.6 Fragments (LMWs) by SDS-PAGE N-Red

The samples showed a time 0 value of LMWs by SDS-PAGE N-RED in the range 11.9-16.2%, followed by stepwise increase at the next point (4 weeks) followed by minor changes over the rest of stability, up to six months (FIG. 17).

5.4.7 Sub-Visible Particles

As for sub-visible particles per container, the counts were below the limits set by United States, European and Japanese Pharmacopoeia for solutions for infusion or injection with nominal content of less than 100 mL (6000 per container equal to or greater than 10 μm and 600 per container equal to or greater than 25 μm). The relevant bar-charts are shown in FIG. 18 and FIG. 19.

No changes in sub-visible particles upon stability at 25° C. were highlighted.

5.4.8 Biological Activity

Bioactivity values were typically in the range 90-110% for all time points tested in the course of the stability study. No decreases observed upon stability at 25° C.

5.4.9 Isoforms Pattern

The results from iCE280 experiments are reported in FIG. 20 (acidic cluster, sum of peaks 1-2-3-4), FIG. 21 (main peak) and FIG. 22 (basic cluster, sum of peaks 6-7). Acidic cluster tends to increase over storage at 25° C. All samples show acidic cluster increase of about +10% after six months at 25° C. and concurrent decrease in main peak (−5% after 6 months) and basic cluster (−5% after 6 months). 5.4.10 25° C. Stability Outcome Over 6-month stability at 25° C., the five formulations tested showed no changes in terms of protein content, appearance, clarity, pH, aggregates, sub-visible particles and bioactivity with respect to time 0.

Fragments were found to increase by +5 percentage points according to SDS-PAGE N-RED after six-months at 25° C., while no statistically significant changes were highlighted by Bioanalyzer.

Similar behavior in isoforms profile by iCE280: acidic cluster of all formulations tend to increase by +10% over the six month-study, with concurrent decreases in main peak and basic cluster.

5.5 Stability at 40° C.

5.5.1 Degree of Coloration by Visual Inspection

No changes observed over stability. All solutions remain clearer than clearest standard solution (<Y7).

5.5.2 Degree of Opalescence by Nephelometry

No changes observed over stability. All solutions show turbidity comprised of 2 NTU (clear solutions range). Values within specifications.

5.5.3 pH

No changes observed over stability. All solutions show pH values in line with target (5.2±0.1 for formulations 1-2-3-4 and 5.5±0.1 for Reference DP). Values within specifications.

5.5.4 Protein Content by OD

Concentration of formulations 1 and 2 (target concentration=20 mg/mL) was found in the range 18.0-19.0 mg/mL (within ±10% limits with respect to target) during the study, with no tendency towards loss in protein over time.

Concentration of formulations 3 and 4 and Reference DP (target concentration=10 mg/mL) was found in the range 9.5-10.0 mg/mL during the study, with no tendency towards loss in protein over time. Values within specifications.

Heat stress is, in conclusion, not detrimental to protein content at the conditions tested (up to 1 month at 40° C.).

5.5.5 Dimers and HMWs by SE-HPLC

No major changes in aggregation were highlighted after 1 month. All values below 1% total aggregates after 1 month (lower than specification limits, that is not more than 5%).

5.5.6 Fragments (LMWs) by SDS-PAGE N-Red, Bioanalyzer

Given the variability of the SDS-PAGE N-RED method (for instance, time 0 values of 11.9 and 14.5 were determined for DP 01-190214 and DP 02-190214 respectively) it can be concluded that no major changes occur during the study at 40° C. (FIG. 23).

5.5.7 Sub-Visible Particles

As for sub-visible particles per container, the counts were abundantly below the limits set by United States, European and JP Pharmacopoeia for solutions for infusion or injection with nominal content of less than 100 mL (6000 per container equal to or greater than 10 μm and 600 per container equal to or greater than 25 μm). Relevant bar charts shown in FIG. 24 and FIG. 25.

No changes in sub-visible particles upon thermal stress were highlighted.

5.5.8 Biological Activity

Bioactivity values were typically in the range 99-120% for all time points tested in the course of the stability study. No decrease observed upon thermal stress in the samples.

5.5.9 Isoforms Pattern

The results from iCE280 experiments are reported in FIG. 26 (acidic cluster, sum of peaks 1-2-3-4), FIG. 27 (main peak) and FIG. 28 (basic cluster, sum of peaks 6-7). Acidic cluster tends to increase over storage at 40° C.

Main peak variations (FIG. 27) confirmed a slightly better stability of new formulas at 10 mg/mL and identical behavior of the remaining compositions.

Results obtained with basic cluster determination confirmed the above described results.

Up to two weeks, similar behavior was observed in the five compositions. At higher stability times, slight differentiation arises between the 20 mg/mL and the 10 mg/mL Avelumab DP (slightly better resistance in formulas at 10 mg/mL).

5.5.10 40° C. Stability Outcome

At 40° C. (1 month), the five formulations tested showed no changes in terms of protein content, appearance, clarity, pH, aggregates, sub-visible particles and bioactivity with respect to time 0.

Small differences between 10 mg/mL and 20 mg/mL DP formulations highlighted by iCE280 (acidic cluster tends to undergo some increase upon storage, slightly more evident in 20 mg/mL than in 10 mg/mL DP formulations).

5.6 Conclusions 5.6.1 Stability at 2-8° C. (12 Months)

All formulations were found to be stable: no significant changes observed in terms of appearance, turbidity (by nephelometry), sub-visible particles, pH, protein content (by OD), aggregation (by SE-HPLC), fragments (by SDS-PAGE N-RED and Bioanalyzer), isoforms profile (by iCE280) and biological activity (by bioassay) with respect to time 0.

5.6.2 Stability at 25° C. (6 Months)

No changes in terms of protein content, appearance, clarity, pH, aggregates, sub-visible particles and bioactivity with respect to time 0.

Fragments were found to increase by +5% according to SDS-PAGE N-RED after six-months at 25° C., while no statistically significant changes were highlighted by Bioanalyzer (a method used as an additional tool to add robustness to conclusions on fragmentation occurrence).

A similar behavior was observed in isoforms profile by iCE280: acidic cluster of all formulations tend to increase by +10% over the six month-study, with concurrent decreases in main peak and basic cluster.

5.6.3 Stability at 40° C. (1 Month)

No changes in terms of protein content, appearance, clarity, pH, aggregates, sub-visible particles and bioactivity with respect to time 0, Small differences between 10 mg/mL and 20 mg/mL DP formulations highlighted by iCE280 (acidic cluster tends to undergo some increase upon storage, slightly more evident in 20 mg/mL than in 10 mg/mL DP formulations)

5.7 Stability Over 24 Months 5.7.1 Manufacturing of DP Compositions

The following DP compositions were manufactured and their stability studied over a period of 24 months:

TABLE 23

DP Compositions

| Ingredient(s) | DP 01-160414 | DP 02-160414 |
| --- | --- | --- |
| avelumab | 20 mg/mL | 20 mg/mL |
| Acetate Acid Glacial (100%) | 0.60 mg/mL * | 0.60 mg/mL * |
| Mannitol | 51 mg/mL | 51 mg/mL |
| Polysorbate 20 | 0.5 mg/mL | 0.5 mg/mL |
| sodium hydroxide | 0.30 mg/mL ** | 0.30 mg/mL ** |
| Filling volume | 10 mL | 30 mL |
| Strength | 200 mg/vial | 600 mg/vial |

* Corresponding to 10 mM Sodium Acetate
** Final pH: 5.2

Both formulations correspond to formulation DP 01-190214 as shown in Table 21. The only difference is that a fixed amount of 0.3 mg/mL (7.5 mM) of sodium hydroxide was used to yield a pH of 5.2 when combined with 0.6 mg/mL glacial acetic acid. The sole difference between formulations DP 01-160414 and DP 02-160414 is that the latter formulation has a volume of 30 mL per vial, while the former has 10 mL per vial.

Both formulations were double-filtered through a 0.22 μm PVDF membrane, followed by the manual filling in vials. Protein content was tested before and after filtration; the relevant results indicate that no loss of protein occurs upon double aseptic filtration Stability data up to 24 months (at +5±3° C.) and up to 6 months at +25° C.±2° C. (RH 60%±5%) have been collected on the two formulations in the respective final containers (vials).

5.7.2 Stability Up to 24 Months (at +5±3° C.)

At +5±3° C., up to 24 months, no changes in protein content (by OD), HMWs (by SE-HPLC), turbidity (by nephelometry), particles formation (by light obscuration), degree of coloration (by visual inspection), and biopotency were observed. Slight increase in acidic isoforms (+5% observed for all compositions after 2 years).

No statistically significant changes were observed in terms of fragmentation by SDS-PAGE N-RED, Bioanalyzer and CE-SDS N-RED.

5.7.3 Stability Up to 6 Months at +25° C.±2° C. (RH 60%±5%)

At +25° C.±2° C. (RH 60%±5%), up to 6 months, no changes in protein content (by OD), HMWs (by SE-HPLC), turbidity (by nephelometry), particles formation (by light obscuration), isoforms profile (by iCE280), degree of coloration (by visual inspection), electrophoretic purity (by SDS/-PAGE RED) and biopotency were observed. Similarly to stability at 5° C., no statistically significant increase in fragmentation was observed at +25° C.±2° C. (RH 60%±5%) (results confirmed by Bioanalyzer).

5.7.4 Holding Time

Holding time before filtration (in bags, up to 24 hours at room temperatures), holding time after filtration (in bags, up to 72 hours at room temperature) and shaking (up to 24 hours at 200 rpm at room temperature) showed no significant changes in protein content, particles formation, aggregates and turbidity, thus indicating no major issues that may arise during standard times of operations typically considered during manufacturing process.

5.7.5 Freeze/Thaw Study

A freeze/thaw study evidenced that the tested formulations can safely be frozen at −80° C. and then allowed to warm up to +5±3° C., or +25° C., with no major changes occurring to the protein.

The invention claimed is:

1. An aqueous pharmaceutical antibody formulation, comprising:
   (i) Avelumab in a concentration of 1 milligram/milliliter (mg/mL) to 30 mg/ml, as the antibody;
   (ii) acetate or histidine in a concentration of 5 millimolar (mM) to 15 mM as the buffering agent;
   (iii) D-mannitol or trehalose in a concentration of 240 mM to 320 mM, or a combination of arginine HCl in a concentration of 50 to 150 mM and glutamic acid in a concentration of 25 mM to 75 mM as a stabiliser; and
   (iv) Poloxamer 188 or Polysorbate 20 in a concentration of 0.25 mg/mL to 0.75 mg/mL, as surfactant, or no surfactant;
   wherein the formulation does not comprise methionine, and further wherein the formulation has a pH of 5.0 to 6.0.

2. The formulation of claim 1, wherein said pH is 5.0 to 5.6.

3. The formulation of claim 1, wherein the concentration of Avelumab is about 10 mg/mL to about 20 mg/mL.

4. The formulation of claim 1, wherein the concentration of said acetate or histidine is about 10 mM.

5. The formulation of claim 1, wherein the concentration of said D-mannitol or trehalose is about 280 mM, or for the said combination of arginine HCl and glutamic acid, the concentration of arginine HCl is about 150 mM and the concentration of glutamic acid is about 50 mM.

6. The formulation of claim 1, wherein the concentration of said Poloxamer 188 or Polysorbate 20 is about 0.5 mg/mL.

7. The formulation of claim 1, wherein said pH is 5.2 (±0.1) to 5.5 (±0.1).

8. The formulation of claim 1, comprising acetate in a concentration of about 10 mM, and not comprising any other buffering agent.

9. The formulation of claim 1, comprising D-mannitol or trehalose in a concentration of about 280 mM, and not comprising any other stabiliser.

10. The formulation of claim 1, comprising Polysorbate 20 or Poloxamer 188 in a concentration of about 0.5 mg/mL, and not comprising any other surfactant.

11. An aqueous pharmaceutical antibody formulation, comprising:
(i) Avelumab in a concentration of about 10 milligram/milliliter (mg/mL) as the antibody;
(ii) acetate in a concentration of about 10 millimolar (mM) as the buffering agent;
(iii) D-mannitol or trehalose in a concentration of about 280 mM as a stabiliser; and
(iv) Polysorbate 20 or Poloxamer 188 in a concentration of about 0.5 mg/mL as surfactant;
wherein the formulation does not comprise methionine, and
further wherein the formulation has a pH of 5.5 (±0.1).

12. The formulation of claim 9, comprising:
(i) Avelumab in a concentration of 10 mg/mL;
(ii) acetate in a concentration of 10 mM;
(iii) D-mannitol or trehalose in a concentration of 280 mM; and
(iv) Polysorbate 20 or Poloxamer 188 in a concentration of 0.5 mg/mL;
wherein the formulation has a pH of 5.5 (±0.1).

13. The formulation of claim 10, consisting of:
(i) Avelumab in a concentration of 10 mg/mL;
(ii) sodium acetate trihydrate in a concentration of 10 mM;
(iii) D-mannitol or trehalose in a concentration of 280 mM;
(iv) Polysorbate 20 or Poloxamer 188 in a concentration of 0.5 mg/mL;
(v) HCl to adjust the pH; and
(vi) water (for injection) as the solvent;
wherein the formulation has a pH of 5.5 (±0.1).

14. The formulation of claim 13, consisting of:
(i) Avelumab in a concentration of 10 mg/mL;
(ii) sodium acetate trihydrate in a concentration of 10 mM;
(iii) trehalose dihydrate in a concentration of 280 mM;
(iv) Polysorbate 20 in a concentration of 0.5 mg/mL;
(v) HCl to adjust the pH; and
(vi) water (for injection) as the diluent;
wherein the formulation has a pH of 5.5 (±0.1).

15. The formulation of claim 11, consisting of:
(i) Avelumab in a concentration of 10 mg/mL;
(ii) sodium acetate trihydrate in a concentration of 10 mM;
(iii) D-mannitol in a concentration of 280 mM;
(iv) Polysorbate 20 in a concentration of 0.5 mg/mL;
(v) HCl to adjust the pH; and
(vi) water (for injection) as the diluent;
wherein the formulation has a pH of 5.5 (±0.1).

16. The formulation of claim 1, comprising:
(i) Avelumab in a concentration of about 20 mg/mL as the antibody;
(ii) acetate in a concentration of about 10 mM as the buffering agent;
(iii) D-mannitol or trehalose in a concentration of about 280 mM as a stabiliser; and
(iv) Polysorbate 20 or Poloxamer 188 in a concentration of about 0.5 mg/mL as surfactant;
wherein the formulation has a pH of 5.2 (±0.1).

17. The formulation of claim 16, comprising:
(i) Avelumab in a concentration of 20 mg/mL;
(ii) acetate in a concentration of 10 mM;
(iii) D-mannitol or trehalose in a concentration of 280 mM; and
(iv) Polysorbate 20 or Poloxamer 188 in a concentration of 0.5 mg/mL;
wherein the formulation has a pH of 5.2 (±0.1).

18. The formulation of claim 1, wherein the formulation does not comprise an antioxidant.

19. The formulation of claim 16, consisting of:
(i) Avelumab in a concentration of 20 mg/mL;
(ii) acetic acid in a concentration of 10 mM;
(iii) D-mannitol or trehalose dihydrate in a concentration of 280 mM;
(iv) Polysorbate 20 or Poloxamer 188 in a concentration of 0.5 mg/mL;
(v) sodium acetate to adjust the pH; and
(vi) water (for injection) as the diluent;
wherein the formulation has a pH of 5.2 (±0.1).

20. The formulation of claim 19, consisting of:
(i) Avelumab in a concentration of 20 mg/mL;
(ii) acetic acid in a concentration of 10 mM;
(iii) D-mannitol in a concentration of 280 mM;
(iv) Polysorbate 20 in a concentration of 0.5 mg/mL;
(v) sodium acetate to adjust the pH; and
(vi) water (for injection) as the diluent;
wherein the formulation has a pH of 5.2 (±0.1).

21. The formulation of claim 19, consisting of:
(i) Avelumab in a concentration of 20 mg/mL;
(ii) acetic acid in a concentration of 10 mM;
(iii) trehalose dihydrate in a concentration of 280 mM;
(iv) Polysorbate 20 in a concentration of 0.5 mg/mL;
(v) sodium acetate to adjust the pH; and
(vi) water (for injection) as the diluent;
wherein the formulation has a pH of 5.2 (±0.1).

22. The formulation of claim 19, consisting of:
(i) Avelumab in a concentration of 20 mg/mL;
(ii) acetic acid in a concentration of 10 mM;
(iii) D-mannitol in a concentration of 280 mM;
(iv) Poloxamer 188 in a concentration of 0.5 mg/mL;
(v) sodium acetate to adjust the pH; and
(vi) water (for injection) as the diluent;
wherein the formulation has a pH of 5.2 (±0.1).

23. The formulation of claim 19, consisting of:
(i) Avelumab in a concentration of 20 mg/mL;
(ii) acetic acid in a concentration of 10 mM;
(iii) trehalose dihydrate in a concentration of 280 mM;
(iv) Poloxamer 188 in a concentration of 0.5 mg/mL;
(v) sodium acetate to adjust the pH; and
(vi) water (for injection) as the diluent;
wherein the formulation has a pH of 5.2 (±0.1).

24. The formulation of claim 16, consisting of:
(i) Avelumab in a concentration of 20 mg/mL;
(ii) acetic acid in a concentration of 10 mM;
(iii) D-mannitol in a concentration of 280 mM;
(iv) Polysorbate 20 in a concentration of 0.5 mg/mL;
(v) sodium hydroxide in a concentration of 7.5 mM; and
(vi) water (for injection) as the diluent;
wherein the formulation has a pH of 5.2 (±0.1).

25. The formulation of claim 24, wherein the formulation is made by combining:
(i) 20 mg/mL of Avelumab;
(ii) 0.6 mg/mL of glacial acetic acid;
(iii) 51 mg/mL of D-mannitol;
(iv) 0.5 mg/mL of Polysorbate 20;
(v) 0.3 mg/mL of sodium hydroxide; and
(vi) water (for injection) as the diluent.

26. The formulation of claim 2, consisting of:
(i) Avelumab in a concentration of 20 mg/mL;
(ii) acetic acid in a concentration of 0.6 mg/mL;
(iii) D-mannitol in a concentration of 51 mg/mL;
(iv) Polysorbate 20 in a concentration of 0.5 mg/mL;
(v) sodium hydroxide in a concentration of 0.3 mg/mL; and
(vi) water (for injection) as the diluent;
wherein the formulation has a pH of 5.0 to 5.6.

27. An aqueous pharmaceutical antibody formulation, consisting of Avelumab in a concentration of 20 milligram/milliliter (mg/mL) as the active ingredient; and glacial acetic acid, D-mannitol, Polysorbate 20, sodium hydroxide and water for injection as the excipients; wherein the formulation has a pH of 5.0 to 5.6.

28. The formulation of claim 27, which has a pH of 5.2 (±0.1).

29. The formulation of claim 1, wherein said Avelumab has the heavy chain sequence of either (SEQ ID NO:1) or (SEQ ID NO:2), the light chain sequence of (SEQ ID NO:3), and carries a glycosylation on Asn300 comprising FA2 and FA2G1 as the main glycan species, having a joint share of more than 70% of all glycan species.

30. The formulation of claim 29, wherein in the Avelumab glycosylation said FA2 has a share of 44% to 54% and said FA2G1 has a share of 25% to 41% of all glycan species.

31. The formulation of claim 30, wherein in the Avelumab glycosylation said FA2 has a share of 47% to 52% and said FA2G1 has a share of 29% to 37% of all glycan species.

32. The formulation of claim 29, wherein in the Avelumab glycosylation said FA2 has a share of about 49% and said FA2G1 has a share of about 30% to about 35% of all glycan species.

33. The formulation of claim 29, wherein the Avelumab glycosylation further comprises as minor glycan species A2 with a share of less than 5%, A2G1 with a share of less than 5%, A2G2 with a share of less than 5% and FA2G2 with a share of less than 7% of all glycan species.

34. The formulation of claim 33, wherein in the Avelumab glycosylation said A2 has a share of 3% to 5%, said A2G1 has a share of less than 4%, said A2G2 has a share of less than 3% and said FA2G2 has a share of 5% to 6% of all glycan species.

35. The formulation of claim 34, wherein in the Avelumab glycosylation said A2 has a share of about 3.5% to about 4.5%, said A2G1 has a share of about 0.5% to about 3.5%, said A2G2 has a share of less than 2.5% and said FA2G2 has a share of about 5.5% of all glycan species.

36. The formulation of claim 29, wherein said Avelumab has the heavy chain sequence of (SEQ ID NO:2).

37. The formulation of claim 1, which is for intravenous (IV) administration.

38. A vial containing the formulation of claim 37.

39. The vial of claim 38, which contains 200 mg Avelumab in 10 mL of solution for a concentration of 20 mg/mL.

40. The vial of claim 38, which is a glass vial.

* * * * *